(12) United States Patent
Fujita et al.

(10) Patent No.: US 9,072,150 B2
(45) Date of Patent: *Jun. 30, 2015

(54) THIADIAZOLE-BASED COMPOUND, LIGHT EMITTING ELEMENT COMPOUND, LIGHT EMITTING ELEMENT, LIGHT EMITTING DEVICE, AUTHENTICATION DEVICE, AND ELECTRONIC APPARATUS

(75) Inventors: Tetsuji Fujita, Chino (JP); Hidetoshi Yamamoto, Suwa (JP)

(73) Assignee: SEIKO EPSON CORPORATION, Tokyo (JP)

( * ) Notice: Subject to any disclaimer, the term of this patent is extended or adjusted under 35 U.S.C. 154(b) by 58 days.

This patent is subject to a terminal disclaimer.

(21) Appl. No.: 13/445,523

(22) Filed: Apr. 12, 2012

(65) Prior Publication Data

US 2012/0262057 A1    Oct. 18, 2012

(30) Foreign Application Priority Data

Apr. 18, 2011    (JP) .................................. 2011-092427

(51) Int. Cl.
*H05B 33/14* (2006.01)
*C07D 513/04* (2006.01)
(Continued)

(52) U.S. Cl.
CPC .............. *H05B 33/14* (2013.01); *C07D 471/04* (2013.01); *C07D 513/04* (2013.01);
(Continued)

(58) Field of Classification Search
None
See application file for complete search history.

(56) References Cited

U.S. PATENT DOCUMENTS 4,769,292 A    9/1988    Tang et al.
5,104,740 A    4/1992    Shinkai et al.
(Continued)

FOREIGN PATENT DOCUMENTS

EP    0 281 381 B1    7/1992
JP    A-63-264692    11/1988
(Continued)

OTHER PUBLICATIONS

Machine English translation of JP 2002-097465 A. Jan. 3, 2014.*
(Continued)

*Primary Examiner* — J. L. Yang
(74) *Attorney, Agent, or Firm* — Oliff PLC

(57) ABSTRACT

A light emitting element includes a light emitting layer that is provided between an anode, a cathode, an anode, and a cathode, and the light emitting layer is configured to include the compound represented by Formula 1 below and the compound represented by Formula RH-1 below.

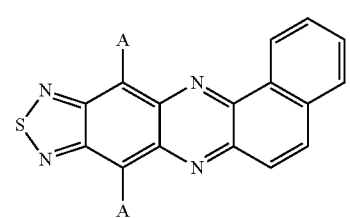

(In Formula 1, A indicates an aryl group, an arylamino group, or triarylamine that may respectively independently include a hydrogen atom, an alkyl group, and a substituent.)

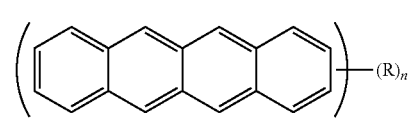

(In Formula IRH-1, n indicates a natural number between 1 and 12, and R represents a substituent or a functional group, and indicates an aryl group or an arylamino group that may respectively independently include a hydrogen atom, an alkyl group, and a substituent.)

19 Claims, 5 Drawing Sheets

(51) Int. Cl.
*C07D 471/04* (2006.01)
*C07D 519/00* (2006.01)
*C09K 11/06* (2006.01)
*H01L 51/00* (2006.01)
*H01L 51/50* (2006.01)

(52) U.S. Cl.
CPC .............. *C07D 519/00* (2013.01); *C09K 11/06* (2013.01); *H01L 51/0061* (2013.01); *H01L 51/0071* (2013.01); *H01L 51/0054* (2013.01); *H01L 51/5012* (2013.01); *H01L 51/5016* (2013.01); *C09K 2211/1007* (2013.01); *C09K 2211/1011* (2013.01); *C09K 2211/1066* (2013.01)

(56) References Cited

U.S. PATENT DOCUMENTS

| | | | |
|---|---|---|---|
| 5,294,869 | A | 3/1994 | Tang et al. |
| 5,449,564 | A | 9/1995 | Nishio et al. |
| 6,004,685 | A | 12/1999 | Antoniadis et al. |
| 6,680,131 | B1 | 1/2004 | Ishibashi et al. |
| 7,632,579 | B2 | 12/2009 | Ise et al. |
| 7,714,099 | B2 | 5/2010 | Morishita et al. |
| 7,902,542 | B2 | 3/2011 | Haase et al. |
| 7,919,773 | B2 | 4/2011 | Kawakami et al. |
| 7,947,992 | B2 | 5/2011 | Yasukawa et al. |
| 7,960,912 | B2 | 6/2011 | Yasukawa et al. |
| 8,039,128 | B2 | 10/2011 | Watanabe et al. |
| 8,803,138 | B2 | 8/2014 | Fujita et al. |
| 2003/0008172 | A1 | 1/2003 | Leclerc et al. |
| 2003/0027016 | A1 | 2/2003 | Ara et al. |
| 2004/0018382 | A1 | 1/2004 | Kinlen |
| 2005/0079381 | A1 | 4/2005 | Hamada et al. |
| 2006/0063027 | A1 | 3/2006 | Vestweber et al. |
| 2006/0154105 | A1 | 7/2006 | Yamamoto et al. |
| 2007/0077453 | A1 | 4/2007 | Sano et al. |
| 2007/0285005 | A1 | 12/2007 | Itai |
| 2008/0061681 | A1 | 3/2008 | Thompson et al. |
| 2008/0067479 | A1 | 3/2008 | Kimura et al. |
| 2008/0230123 | A1 | 9/2008 | Mitsui et al. |
| 2009/0079335 | A1 | 3/2009 | Mitsuya et al. |
| 2009/0091250 | A1 | 4/2009 | Yasukawa et al. |
| 2009/0115348 | A1* | 5/2009 | Yamazaki et al. ............. 315/297 |
| 2009/0243476 | A1 | 10/2009 | Nomura et al. |
| 2009/0261360 | A1 | 10/2009 | Yasukawa et al. |
| 2010/0133434 | A1 | 6/2010 | Meng et al. |
| 2010/0155694 | A1 | 6/2010 | Miller et al. |
| 2010/0237338 | A1 | 9/2010 | Yamamoto et al. |
| 2010/0237990 | A1 | 9/2010 | Amano et al. |
| 2010/0244671 | A1 | 9/2010 | Nomura et al. |
| 2010/0244679 | A1 | 9/2010 | Fujita et al. |
| 2010/0317858 | A1 | 12/2010 | Konno |
| 2011/0087034 | A1 | 4/2011 | Miyata et al. |
| 2011/0253988 | A1 | 10/2011 | Molt et al. |
| 2011/0279020 | A1 | 11/2011 | Inoue et al. |
| 2011/0303901 | A1 | 12/2011 | Cheng et al. |
| 2012/0056213 | A1 | 3/2012 | Yamamoto et al. |
| 2012/0091923 | A1 | 4/2012 | Kastner-Jung et al. |
| 2012/0262057 | A1 | 10/2012 | Fujita et al. |
| 2012/0267615 | A1 | 10/2012 | Fujita et al. |
| 2013/0009909 | A1 | 1/2013 | Yamazaki et al. |
| 2013/0032791 | A1 | 2/2013 | Bazan et al. |
| 2013/0037784 | A1 | 2/2013 | Yamamoto et al. |
| 2013/0037785 | A1* | 2/2013 | Fujita et al. ..................... 257/40 |
| 2013/0099209 | A1 | 4/2013 | Hartmann et al. |
| 2013/0168654 | A1* | 7/2013 | Fujita et al. ..................... 257/40 |
| 2013/0221334 | A1 | 8/2013 | Yamamoto et al. |

FOREIGN PATENT DOCUMENTS

| | | | |
|---|---|---|---|
| JP | A-2-255788 | 10/1990 | |
| JP | A-3-791 | 1/1991 | |
| JP | A-3-792 | 1/1991 | |
| JP | A-3-162481 | 7/1991 | |
| JP | A-3-177486 | 8/1991 | |
| JP | A-5-32966 | 2/1993 | |
| JP | A-5-214334 | 8/1993 | |
| JP | A-5-258859 | 10/1993 | |
| JP | A-6-73374 | 3/1994 | |
| JP | A-6-93257 | 4/1994 | |
| JP | A-6-136359 | 5/1994 | |
| JP | A-6-145146 | 5/1994 | |
| JP | A-6-240246 | 8/1994 | |
| JP | A-10-330295 | 12/1998 | |
| JP | A-11-233261 | 8/1999 | |
| JP | A-2000-91073 | 3/2000 | |
| JP | 2001-097949 A | 4/2001 | |
| JP | A-2001-110570 | 4/2001 | |
| JP | 2002097465 A * | 4/2002 | ............. C09K 11/06 |
| JP | A-2003-055652 | 2/2003 | |
| JP | 2003-109760 A | 4/2003 | |
| JP | 2004-002297 A | 1/2004 | |
| JP | A-2005-063938 | 3/2005 | |
| JP | 2005-531552 A | 10/2005 | |
| JP | 2006-045398 A | 2/2006 | |
| JP | 2006-511939 A | 4/2006 | |
| JP | A-2007-115626 | 5/2007 | |
| JP | 2008-069100 A | 3/2008 | |
| JP | A-2009-016693 | 1/2009 | |
| JP | 2009-049094 A | 3/2009 | |
| JP | 2009-256343 A | 11/2009 | |
| JP | 2010-147179 A | 7/2010 | |
| JP | 2010-254674 A | 11/2010 | |
| WO | 03-095445 A | 11/2003 | |
| WO | 2004-058911 A2 | 7/2004 | |
| WO | WO 2008/069322 A1 | 6/2008 | |

OTHER PUBLICATIONS

Jeff D. Debad et al.; Dibenzotetraphenylperiflanthene: Synthesis, Photophysical Properties, and Electrogenerated Chemiluminescence; Journal American Chemical Society; 1996; vol. 118; pp. 2374-2379.

Mitsuo Kawabe et al.; Electroluminescence of Green Light Region in Doped Anthracene; Japan Journal Appl. Phys. vol. 10; (1971); pp. 527-529.

Du et al., "Efficient Non-Doped Near Infrared Organic Light-Emitting Devices Based on Fluorophores with Aggregation-Induced Emission Enhancement," Chemistry of Materials, vol. 24 (2012) pp. 2178-2185.

Kajii et al., "Visible to Near-Infrared Organic Light-Emitting Diodes Using Phosphorescent Materials by Solution Process," Thin Solid Films, vol. 518 (2009) pp. 551-554.

Qian, et al., "Synthesis and Application of Thiadiazoloquinoxaline-Containing Chromophores as Dopants for Efficient Near-Infrared Organic Light-Emitting Diodes," J. Phys. Chem. C, vol. 113 (2009) pp. 1589-1595.

Aug. 15, 2014 Office Action issued in U.S. Appl. No. 13/564,384.
Aug. 21, 2014 Office Action issued in U.S. Appl. No. 13/564,376.
Mar. 26, 2014 Notice of Allowance issued in U.S. Appl. No. 13/727,339.
Oct. 3, 2014 Office Action issued in U.S. Appl. No. 14/319,410.
Pending U.S. Appl. No. 14/319,410, filed on Jun. 30, 2014.
Pending U.S. Appl. No. 13/773,033, filed on Feb. 21, 2013.
Pending U.S. Appl. No. 13/564,384, filed on Aug. 1, 2012.
Pending U.S. Appl. No. 13/564,376, filed on Aug. 1, 2012.
Pending U.S. Appl. No. 14/055,241, filed on Oct. 16, 2013.
Pending U.S. Appl. No. 13/444,107, filed on Apr. 11, 2012,.
Jan. 22, 2015 Office Action issued in U.S. Appl. No. 13/564,384.
Apr. 22, 2015 Office Action issued in U.S. Appl. No. 13/773,033.
U.S. Appl. No. 14/693,484, filed Apr. 22, 2015 in the name of Yamamoto et al.
U.S. Appl. No. 14/700,751, filed Apr. 30, 2015 in the name of Fujita et al.

\* cited by examiner

LIGHT EMITTING WAVEFORM OF EXAMPLE 1

LIGHT EMITTING WAVEFORM OF SAMPLE EXAMPLE

THIADIAZOLE-BASED COMPOUND, LIGHT EMITTING ELEMENT COMPOUND, LIGHT EMITTING ELEMENT, LIGHT EMITTING DEVICE, AUTHENTICATION DEVICE, AND ELECTRONIC APPARATUS

BACKGROUND

1. Technical Field

The present invention relates to a thiadiazole-based compound, a light emitting element compound, a light emitting element, a light emitting device, an authentication device, and an electronic apparatus.

2. Related Art

An organic electroluminescence element (a so-called organic EL element) is a light emitting element with a structure in which at least one layer of a light emitting organic layer is inserted between an anode and a cathode. With such a light emitting element, by applying an electric field between the anode and the cathode, electrons are injected into a light emitting layer from the cathode side and holes are inserted from the anode side, excitons are generated by the electrons and the holes recoupling within the light emitting layer, and the energy of the excitons when the excitons return to the ground state is released as light.

As such a light emitting element, there are those that emit light at wavelength bands exceeding 700 nm (for example, refer to JP-A-2000-091073 and JP-A-2001-110570).

For example, with the light emitting elements described in JP-A-2000-091073 and JP-A-2001-110570, the light emitting wavelengths are increased by using a material in which an amine group that is an electron donor and a nitrile group that is an electron acceptor coexist as functional groups within a molecule as a dopant of a light emitting layer.

However, with the related art, it was not possible to realize an element that emits light at near-infrared bands with high efficiency and long life.

Further, the realization of an element that surface-emits light at near-infrared bands with high efficiency and long life as the light source for biometric authentication of authenticating individuals using biometric information such as, for example, veins and fingerprints is in demand.

SUMMARY

An advantage of some aspects of the invention is that a thiadiazole-based compound, a light emitting element compound, a light emitting element that emits light at near-infrared bands with high efficiency and long life, a light emitting device, an authentication device, and an electronic apparatus that include the light emitting element are provided.

A thiadiazole-based compound of an aspect of the invention is represented by Formula 2 below.

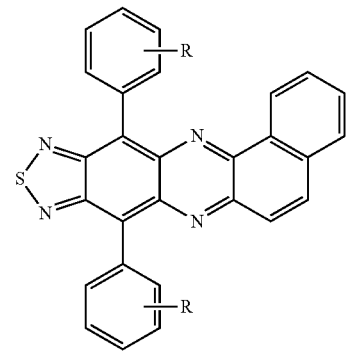

(2)

(In Formula 2, R indicates an aryl group, a diarylamino group, or triarylamine that may respectively independently include a hydrogen atom, an alkyl group, and a substituent.)

In a case when such a thiadiazole-based compound is used as the light emitting material of an organic EL element, for example, the thiadiazole-based compound can be made to emit light at near-infrared bands.

A thiadiazole-based compound of an aspect of the invention is represented by Formula 3 below.

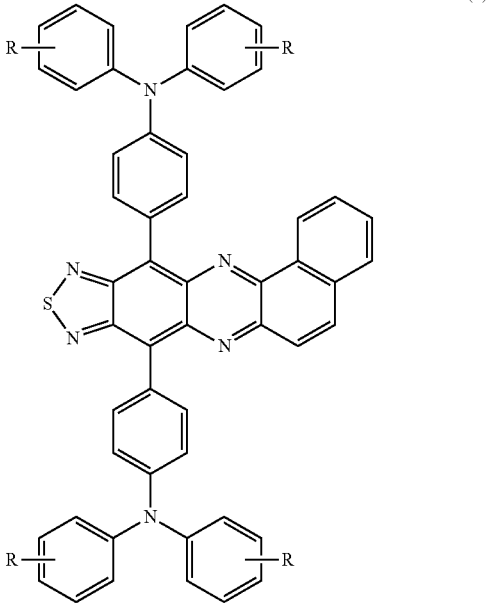

(3)

(In Formula 3, R indicates an aryl group that may respectively independently include a hydrogen atom, an alkyl group, and a substituent. Further, the carbon atoms of two adjacent Rs may be cyclic through being coupled.)

In a case when such a thiadiazole-based compound is used as the light emitting material of an organic EL element, for example, the thiadiazole-based compound can be made to emit light at near-infrared bands.

A thiadiazole-based compound of an aspect of the invention is represented by Formula 4 below.

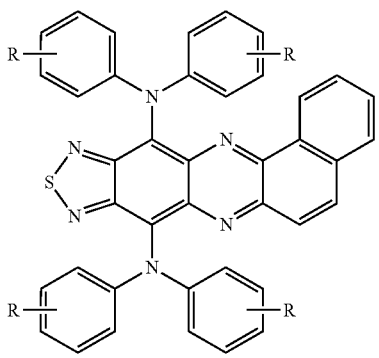

(4)

(In Formula 4, R indicates an aryl group that may respectively independently include a hydrogen atom, an alkyl group, and a substituent. Further, the carbon atoms of two adjacent Rs may be cyclic through being coupled.)

In a case when such a thiadiazole-based compound is used as the light emitting material of an organic EL element, for example, the thiadiazole-based compound can be made to emit light at near-infrared bands.

A light emitting element compound of an aspect of the invention is configured of the thiadiazole-based compound of the invention.

When such a light emitting element compound is used as a light emitting material, for example, the light emitting element compound can be made to emit light at near-infrared bands.

A light emitting element of an aspect of the invention includes: an anode; a cathode; and a light emitting layer that is provided between the anode and the cathode and that emits light through the passage of an electric current between the anode and the cathode, wherein the light emitting element includes the compound represented by Formula 1 below as a light emitting material and includes the compound represented by Formula IRH-1 below as a host material that retains the light emitting material.

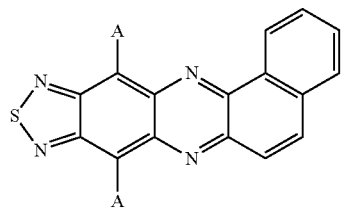

(1)

(In Formula 1, A indicates an aryl group, an arylamino group, or triarylamine that may respectively independently include a hydrogen atom, an alkyl group, and a substituent.)

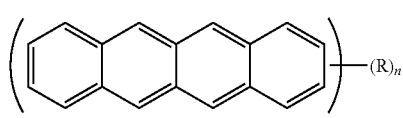

IRH-1

(In Formula IRH-1, n indicates a natural number between 1 and 12, and R represents a substituent or a functional group, and indicates an aryl group or an arylamino group that may respectively independently include a hydrogen atom, an alkyl group, and a substituent.)

According to the light emitting element configured in such a manner, since the compound represented by Formula 1 described above can be used as the light emitting material, light emission at wavelength bands of equal to or greater than 700 nm (near-infrared bands) can be obtained.

Further, since a tetracene-based compound is used as the host material, energy can be effectively transferred from the host material to the light emitting material. The light emitting efficiency of the light emitting element can therefore be made excellent.

Further, since a tetracene-based material is excellent in stability (resistance) with respect to electrons and holes, the life of the light emitting layer and the light emitting element can be increased.

With the light emitting element of the aspect of the invention, it is preferable that the light emitting layer be configured to include the compound represented by Formula IRH-2 below as the host material.

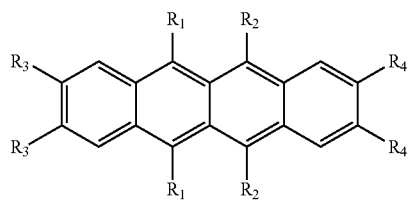

IRH-2

(In Formula IRH-2, $R_1$ to $R_4$ indicate aryl groups or arylamino groups that may respectively independently include a hydrogen atom, an alkyl group, and a substituent. Further, $R_1$ to $R_4$ may be the same as or different from one another.)

In so doing, it is possible to suppress an increase in the voltage during continuous driving, and in addition to increasing the light emitting efficiency of the light emitting element, the life of the light emitting element can be increased.

With the light emitting element of the aspect of the invention, it is preferable that the light emitting layer be configured to include the compound represented by Formula IRH-3 below as the host material.

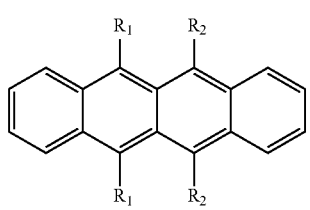

IRH-3

(In Formula IRE-3, $R_1$ and $R_2$ indicate aryl groups or arylamino groups that may respectively independently include a hydrogen atom, an alkyl group, and a substituent. Further, $R_1$ and $R_2$ may be the same as or different from each another.)

In so doing, it is possible to suppress an increase in the voltage during continuous driving, and in addition to increasing the light emitting efficiency of the light emitting element, the life of the light emitting element can be increased.

With the light emitting element of the aspect of the invention, it is preferable that the host material be configured by carbon atoms and hydrogen atoms.

In so doing, it is possible to prevent spontaneous interactions between the host material and the light emitting material. It is therefore possible to increase the light emitting efficiency of the light emitting element. Further, the resistance of the host material with respect to electrons and holes can be increased. The life of the light emitting element can therefore be increased.

A light emitting device of an aspect of the invention includes the light emitting element according to the above-described aspects of the invention.

Light emission at near-infrared bands is possible with such a light emitting device. Further, since the light emitting device includes a light emitting element with high efficiency and long life, the light emitting device has excellent reliability.

An authentication device of the invention includes the light emitting element according to the above-described aspects of the invention.

Such an authentication device can perform biometric authentication using near-infrared light. Further, since the authentication device includes a light emitting element with high efficiency and long life, the authentication device has excellent reliability.

An electronic apparatus of the invention includes the light emitting element according to the above-described aspects of the invention.

Since such an electronic apparatus includes a light emitting element with high efficiency and long life, the electronic apparatus has excellent reliability.

BRIEF DESCRIPTION OF THE DRAWINGS

The invention will be described with reference to the accompanying drawings, wherein like numbers reference like elements.

DESCRIPTION OF EXEMPLARY EMBODIMENTS

Preferable aspects of the thiadiazole-based compound, the light emitting element compound, the light emitting element, the light emitting device, the authentication device, and the electronic apparatus of the invention which are illustrated in the attached drawings will be described below.

Figure 1:
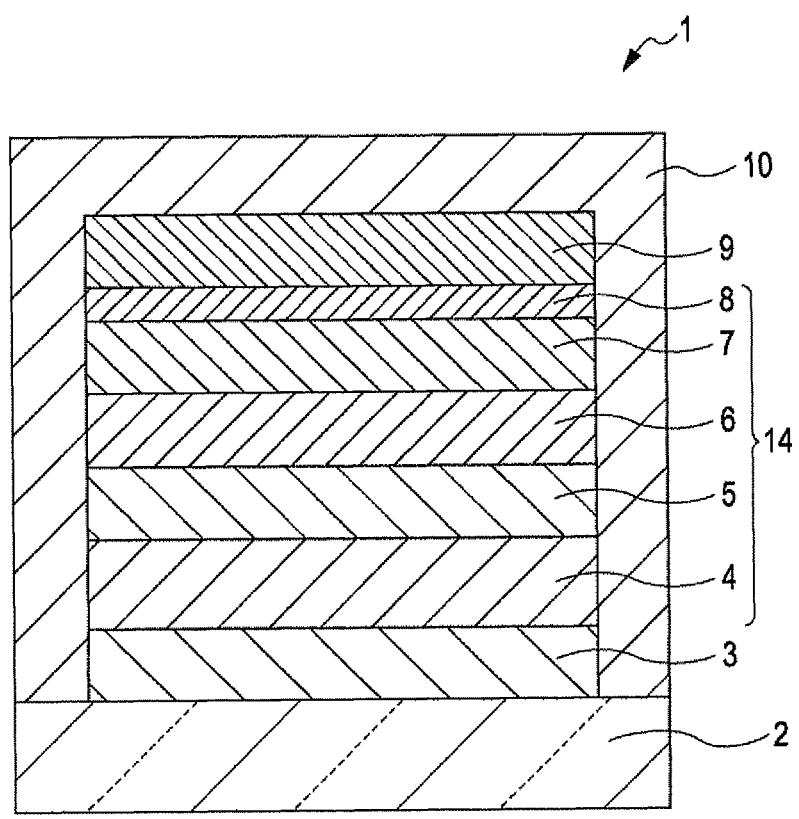
FIG. 1 is a diagram that schematically illustrates a longitudinal section of a light emitting element according to an aspect of the invention.

FIG. 1 is a cross-sectional diagram that schematically illustrates a light emitting element according to an aspect of the invention. Here, for convenience of description, description will be made below with the upper side of FIG. 1 as "top" and the lower side as "bottom".

A light emitting element (electroluminescence element) 1 illustrated in FIG. 1 includes an anode 3, a hole injection layer 4, a hole transport layer 5, a light emitting layer 6, an electron transport layer 7, an electron injection layer 8, and a cathode 9 that are laminated in such an order. That is, the light emitting element 1 has a laminated body 14 in which the hole injection layer 4, the hole transport layer 5, the light emitting layer 6, the electron transport layer 7, and the electron injection layer 8 are laminated in such an order from the anode 3 side to the cathode 9 side between the anode 3 and the cathode 9.

Furthermore, the entirety of the light emitting element 1 is provided on a substrate 2 and sealed by a sealing member 10.

With such a light emitting element 1, by a driving voltage being applied to the anode 3 and the cathode 9, electrons are supplied (injected) from the cathode 9 side and holes are supplied (injected) from the anode 3 side respectively to the light emitting layer 6. Furthermore, the holes and the electrons are recoupled at the light emitting layer 6, excitons are generated by the energy that is released during such recoupling, and energy (fluorescence or phosphorescence) is released (emitted as light) when the excitons return to the ground state. The light emitting element 1 thus emits light.

In particular, the light emitting element 1 emits light at near-infrared bands by using the thiadiazole-based compound (light emitting element compound) as the light emitting material of the light emitting layer 6 as described later. Here, "near-infrared bands" in the present specification refers to wavelength bands that are equal to or greater than 700 nm and equal to or less than 1500 nm.

The substrate 2 supports the anode 3. Since the light emitting element 1 of the present aspect has a configuration of taking out light from the substrate 2 side (bottom emission type), the substrate 2 and the anode 3 are respectively substantially transparent (colorless and transparent, colored and transparent, or semitransparent).

Examples of the constituent material of the substrate 2 include resin materials such as polyethylene terephthalate, polyethylene naphthalate, polypropylene, a cycloolefin polymer, polyamide, polyether sulfone, polymethyl methacrylate, polycarbonate, and polyarylate, glass materials such as quartz glass or soda glass, and the like, and one or two or more types thereof may be used in combination.

While the average thickness of such a substrate 2 is not particularly limited, approximately 0.1 to 30 mm is preferable, and approximately 0.1 to 10 mm is more preferable.

Here, in a case when the light emitting element 1 has a configuration in which light is taken out from the opposite side to the substrate 2 (top emission type), a transparent substrate or an opaque substrate may be used as the substrate 2.

Examples of an opaque substrate include a substrate that is configured by a ceramic material such as alumina, one that has an oxide film (insulating film) formed on the surface of a metallic substrate such as stainless steel, a substrate that is configured by a resin material, and the like.

Further, with such a light emitting element 1, the distance between the anode 3 and the cathode 9 (that is, the average thickness of the laminated body 14) is preferably from 100 to 500 nm, more preferably from 100 to 300 nm, and still more preferably 100 to 250 nm. In so doing, the driving voltage of the light emitting element 1 can be made to be within a practical range easily and securely.

Each of the portions that configure the light emitting element 1 will be successively described below.

Anode

The anode 3 is an electrode that injects holes into the hole transport layer 5 via the hole injection layer 4 described later. A material with a large work function and which is excellent in conductivity is preferable as the constituent material of the anode 3.

Examples of the constituent material of the anode 3 include oxides such as ITO (Indium Tin Oxide), IZO (Indium Zinc Oxide), $In_2O_3$, $SnO_2$, Sb-containing $SnO_2$, and Al-containing ZnO, Au, Pt, Ag, Cu, or an alloy including the above, and one or two or more types thereof may be used in combination.

In particular, it is preferable that the anode 3 be configured by ITO. ITO is a material that is transparent, has a large work function, and is excellent in conductivity. In so doing, holes can be effectively injected from the anode 3 into the hole injection layer 4.

Further, it is preferable that a plasma process is performed on the face of the anode 3 on the hole injection layer 4 side (upper face in FIG. 1). In so doing, the chemical and mechanical stability of the joining face of the anode 3 and the hole injection layer 4 can be increased. As a result, the hole injectability from the anode 3 into the hole injection layer 4 can be improved. Here, such a plasma process will be described in detail in the description of the manufacturing method of the light emitting element 1 described later.

While the average thickness of such an anode 3 is not particularly limited, approximately 10 to 200 nm is preferable, and approximately 50 to 150 nm is more preferable.

Cathode

On the other hand, the cathode 9 is an electrode that injects electrons into the electron transport layer 7 via the electron injection layer 8 described later. It is preferable that a material with a small work function be used as the constituent material of the cathode 9.

Examples of the constituent material of the cathode 9 include Li, Mg, Ca, Sr, La, Ce, Er, Eu, Sc, Y, Yb, Ag, Cu, Al, Cs, Rb, or an alloy including the above, and the like, and one or two or more types thereof may be used in combination (for example, as a laminated body of a plurality of layers, a mixed layer of a plurality of types, or the like).

In particular, in a case when an alloy is used as the constituent material of the cathode 9, an alloy that includes a stable metallic element such as Ag, Al, or Cu, specifically, an alloy such as MgAg, AlLi, and CuLi is preferable. By using such an alloy as the constituent material of the cathode 9, the electron injection efficiency and the safety of the cathode 9 can be improved.

While the average thickness of such a cathode 9 is not particularly limited, approximately 100 to 10000 nm is preferable, and approximately 100 to 500 nm is more preferable.

Here, since the light emitting element 1 of the present aspect is a bottom emission type, light transmissivity is not particularly required of the cathode 9. Further, in the case of a top emission type, since it is necessary for light to be transmitted from the cathode 9 side, the average thickness of the cathode 9 is preferably approximately 1 to 50 nm.

Hole Injection Layer

The hole injection layer 4 has the function of improving the hole injection efficiency from the anode 3 (that is, has hole injectability).

By providing the hole injection layer 4 between the anode 3 and the hole transport layer 5 in such a manner, the hole injectability from the anode 3 is improved, and as a result, the light emitting efficiency of the light emitting element 1 can be increased.

The hole injection layer 4 includes a material with hole injectability (that is, a hole injectable material).

While the hole injectable material that is included in the hole injection layer 4 is not particularly limited, examples thereof include copper phthalocyanine, 4,4'4''-tris(N,N-phenyl-3-methyl-phenylamino)triphenylamine (m-MTDATA), N,N'-bis-(4-diphenyl-amino-phenyl)-N,N'-diphenyl-biphenyl-4-4'-diamine, and the like.

Among such materials, an amine-based material is preferably used as the hole injectable material that is included in the hole injection layer 4 from the viewpoint that an amine-based material has excellent hole injectability and hole transportability, and a diaminobenzene derivative, a benzidine derivative (material including a benzidine skeleton), a triamine-based compound including both a "diaminobenzene" unit and a "benzidine" unit within a molecule, or a tetraamine-based compound is more preferably used.

While the average thickness of such a hole injection layer 4 is not particularly limited, approximately 5 to 90 nm is preferable, and approximately 10 to 70 nm is more preferable.

Here, the hole injection layer 4 may be omitted depending on the constituent materials of the anode 3 and the hole transport layer 5.

Hole Transport Layer

The hole transport layer 5 has a function of transporting the holes that are injected from the anode 3 via the hole injection layer 4 to the light emitting layer 6 (that is, has hole transportability).

The hole transport layer 5 is configured to include a material with hole transportability (that is, a hole transportable material).

Various p type high-molecular materials and various p type low-molecular materials may be used alone or in combination as the hole transportable material that is included in the hole transport layer 5, and examples of such materials include tetraaryl benzidine derivatives such as N,N'-di(1-naphthyl)-N,N'-diphenyl-1,1'-diphenyl-4,4'-diamine (NPD) and N,N'-diphenyl-N,N'-bis(3-methylphenyl)-1,1'-diphenyl-4,4'-diamine (TPD), a tetraaryl diaminofluorene compound or a derivative thereof (amine-based compound), and the like, and one or two or more types thereof may be used in combination.

Among such materials, an amine-based material is preferably used as the hole transportable material that is included in the hole transport layer 5 from the viewpoint that an amine-based material has excellent hole injectability and hole transportability, and a benzidine derivative (material including a benzidine skeleton) is more preferably used.

While the average thickness of such a hole transport layer 5 is not particularly limited, approximately 5 to 90 nm is preferable, and approximately 10 to 70 nm is more preferable.

Light Emitting Layer

The light emitting layer 6 emits light through a current being passed between the anode 3 and the cathode 9 described above.

Such a light emitting layer 6 is configured to include a light emitting material.

In particular, the light emitting layer 6 is configured to include the compound represented by formula 1 below (hereinafter referred to as a "thiadiazole-based compound") as the light emitting material.

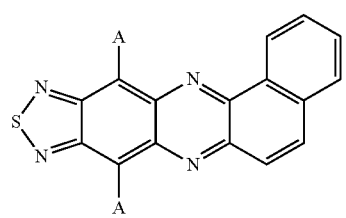

(1)

(In Formula 1, A indicates an aryl group, an arylamino group, or triarylamine that may respectively independently include a hydrogen atom, an alkyl group, and a substituent.)

The light emitting layer 6 that includes the thiadiazole-based compound can obtain light emission at wavelength bands of equal to or greater than 700 nm (near-infrared bands).

Further, as the light emitting material used for the light emitting layer 6, the compounds represented by Formulae 2 to 4 below are preferably used, and specifically, in particular, the compounds represented by Formulae D-1 to D-3 are preferably used.

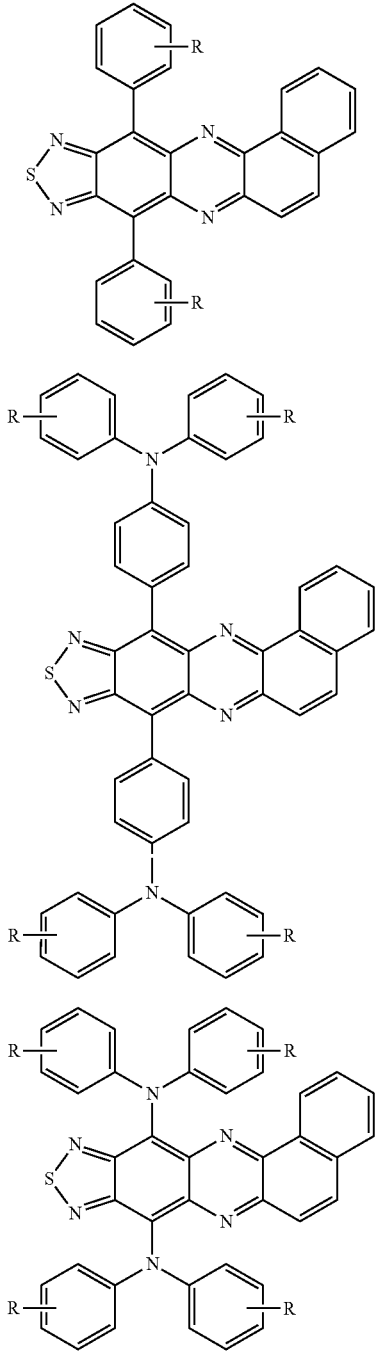

(In Formulae 2 to 4, R indicates an aryl group that may respectively independently include a hydrogen atom, an alkyl group, and a substituent. Further, the carbon atoms of two adjacent Rs may be cyclic through being coupled.)

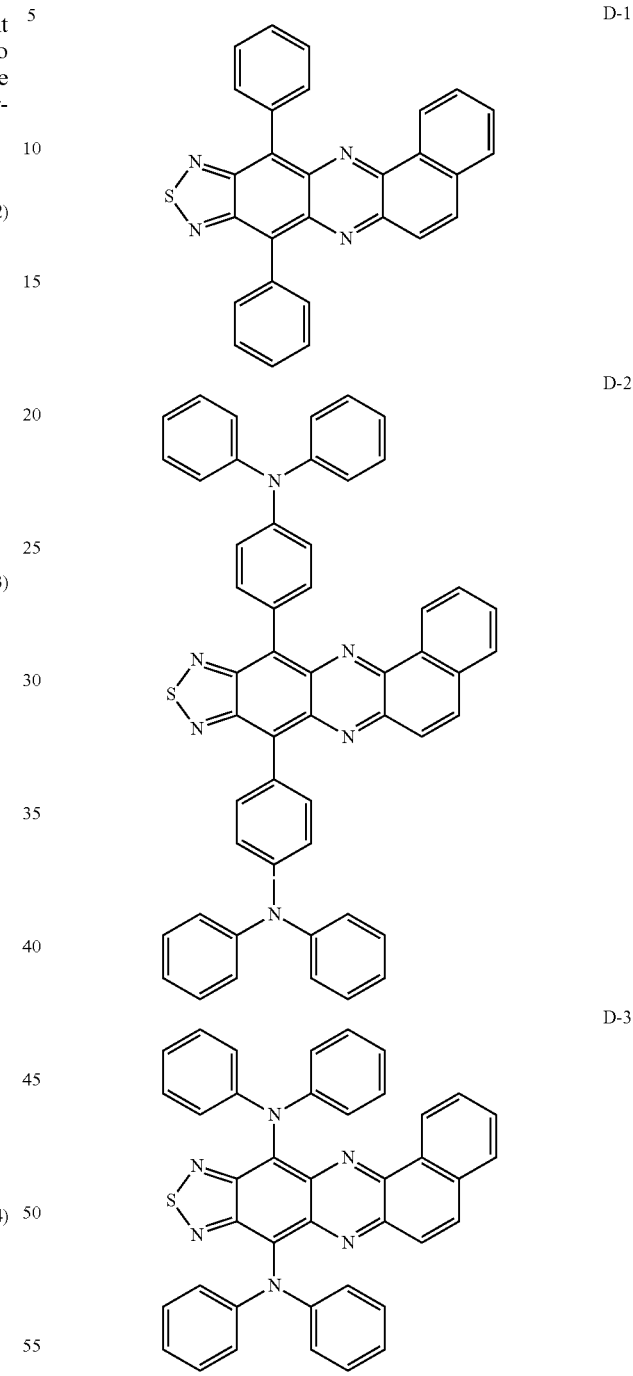

Here, the light emitting layer 6 may also include a light emitting material other than the light emitting materials described above (various fluorescent materials, various phosphorescent materials).

Further, in addition to the light emitting materials described above, a host material in which such light emitting materials are added (supported) as a guest material (dopant) may be used as the constituent material of the light emitting layer 6. The host material generates excitons by recoupling holes and electrons and has a function of exciting the light emitting material by transferring (Förster transfer or Dexter transfer) the energy of the excitons to the light emitting material. It is therefore possible to increase the light emitting efficiency of the light emitting element 1. Such a host material can be used, for example, by doping the light emitting material that is the guest material as the dopant to the host material.

In particular, a tetracene-based material that is an acene-based material may be used as such a host material. If the host material of the light emitting layer 6 is configured to include an acene-based material, electrons can be efficiently passed over from the electron transportable material within the electron transport layer 7 to the scene-based material within the light emitting layer 6.

An scene-based material has little spontaneous interaction with the light emitting material described above. Further, if an acene-based material (particularly a tetracene-based material) is used as the host material, energy transfer from the host material to the light emitting material can be performed efficiently. It is considered that the reason is that (a) generation of the light emitting material in a singlet excited state by the energy transfer of the scene-based material in a triplet excited state, (b) the overlap between the π electron cloud of the acene-based material and the electron cloud of the light emitting material increases, (c) the overlap between the fluorescence spectrum of the acene-based material and the absorption spectrum of the light emitting material increases, and the like.

For such reasons, if an acene-based material is used as the host material, the light emitting efficiency of the light emitting element 1 can be increased.

Further, an acene-based material has excellent resistance to electrons and holes. Furthermore, an acene-based material also has excellent heat stability. It is therefore possible to increase the life of the light emitting element 1. Further, since an acene-based material has excellent thermal stability, in a case when the light emitting layer is formed using a gaseous phase film formation method, the decomposition of the host material due to the heat of the film formation can be prevented. It is therefore possible to form a light emitting layer with an excellent film quality, and as a result, even in such a regard, the light emitting efficiency and the life of the light emitting element 1 can be increased.

Furthermore, since an acene-based material itself does not easily emit light, the host material can be prevented from negatively influencing the light emitting spectrum of the light emitting element 1.

Further, if a tetracene derivative (tetracene-based material) is used as such an acene-based material, electrons can be efficiently passed over from the anthracene skeleton portion of the electron transportable material within the electron transport layer 7 to the tetracene-based material within the light emitting layer 6.

While the tetracene-based material is not particularly limited as long as there is at least one tetracene skeleton within one molecule and the function as the host material as described above can be exhibited, the compound represented by Formula IRH-1 below is preferably used, for example, the compound represented by IRH-2 below is more preferably used, and the compound represented by IRH-3 below is still more preferably used. In so doing, it is possible to suppress a rise in the voltage during continuous driving, the light emitting efficiency of the light emitting element 1 can be increased, and the life of the light emitting element 1 can be increased.

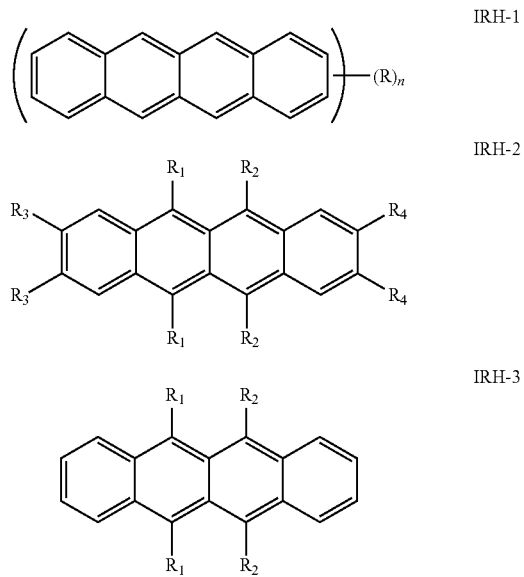

(In Formula IRH-1, n indicates a natural number between 1 and 12, and R represents a substituent or a functional group, and indicates an aryl group or an arylamino group that may respectively independently include a hydrogen atom, an alkyl group, and a substituent. Further, in Formulae IRH-2 and IRH-3, $R_1$ to $R_4$ indicate aryl groups or arylamino groups that may respectively independently include a hydrogen atom, an alkyl group, and a substituent. Further, $R_1$ to $R_4$ may be the same as or different from one another.)

Further, it is preferable that the tetracene-based material that is used as the host material be configured of carbon atoms and hydrogen atoms. In so doing, spontaneous interactions between the host material and the light emitting material can be prevented from taking place. It is therefore possible to increase the light emitting efficiency of the light emitting element 1. Further, the durability of the host material to electrons and holes can be increased. It is therefore possible to suppress a rise in the voltage during continuous driving, and the life of the light emitting element 1 can be increased.

Specifically, for example, the compounds represented by Formulae H1-1 to H1-11 below and the compounds represented by H1-12 to H1-27 below are preferably used as the tetracene-based material.

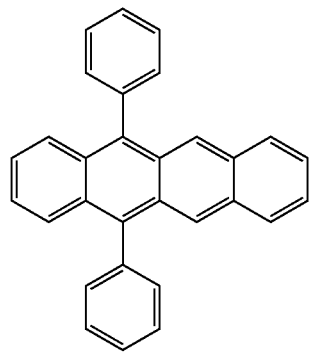

H1-2
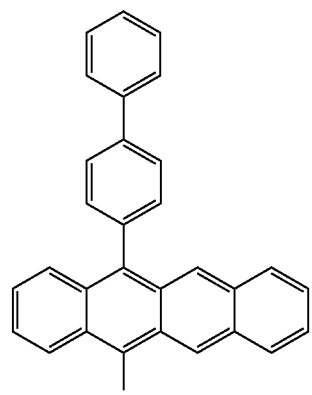
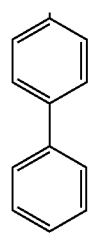
H1-3
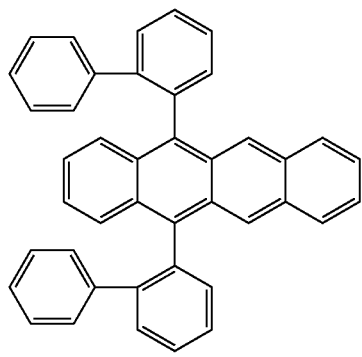
H1-4
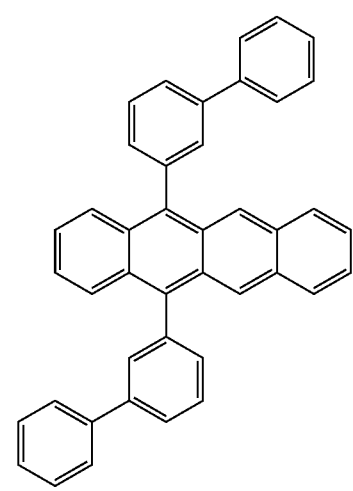
H1-5
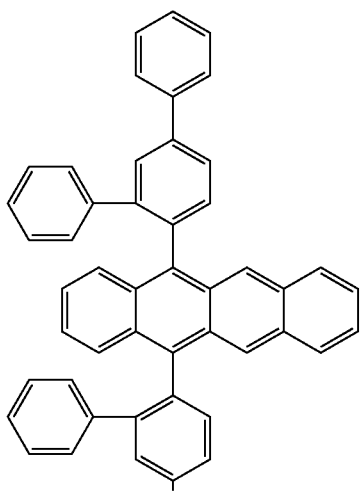
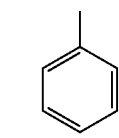
H1-6
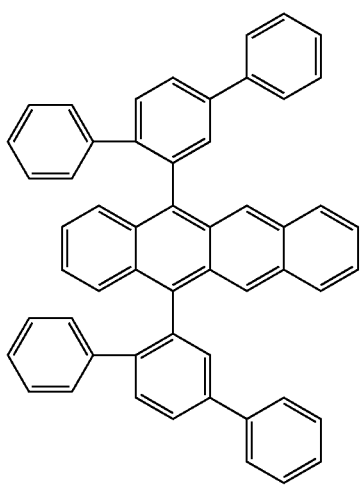
H1-7
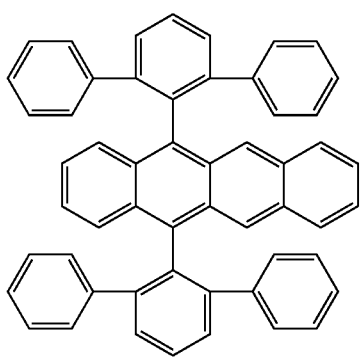

H1-8
H1-9
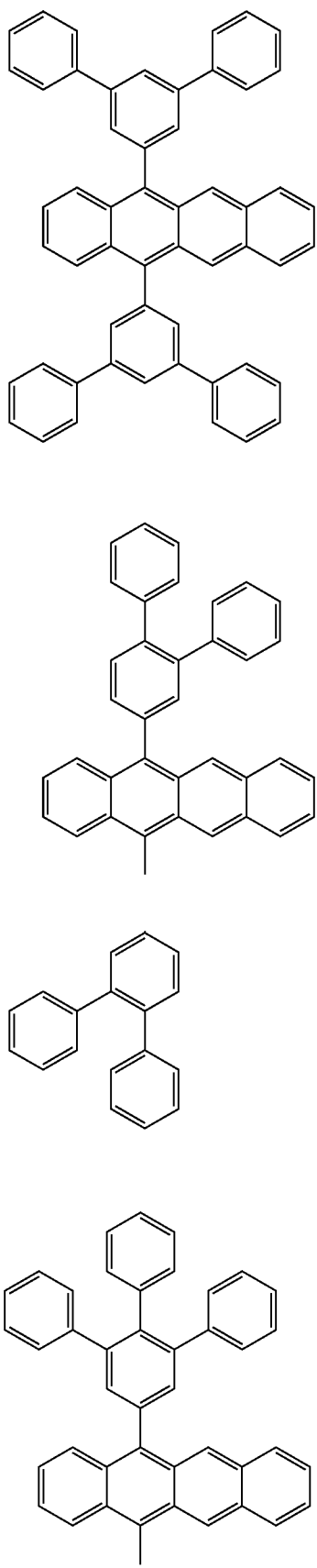
H1-10
H1-11
H1-12
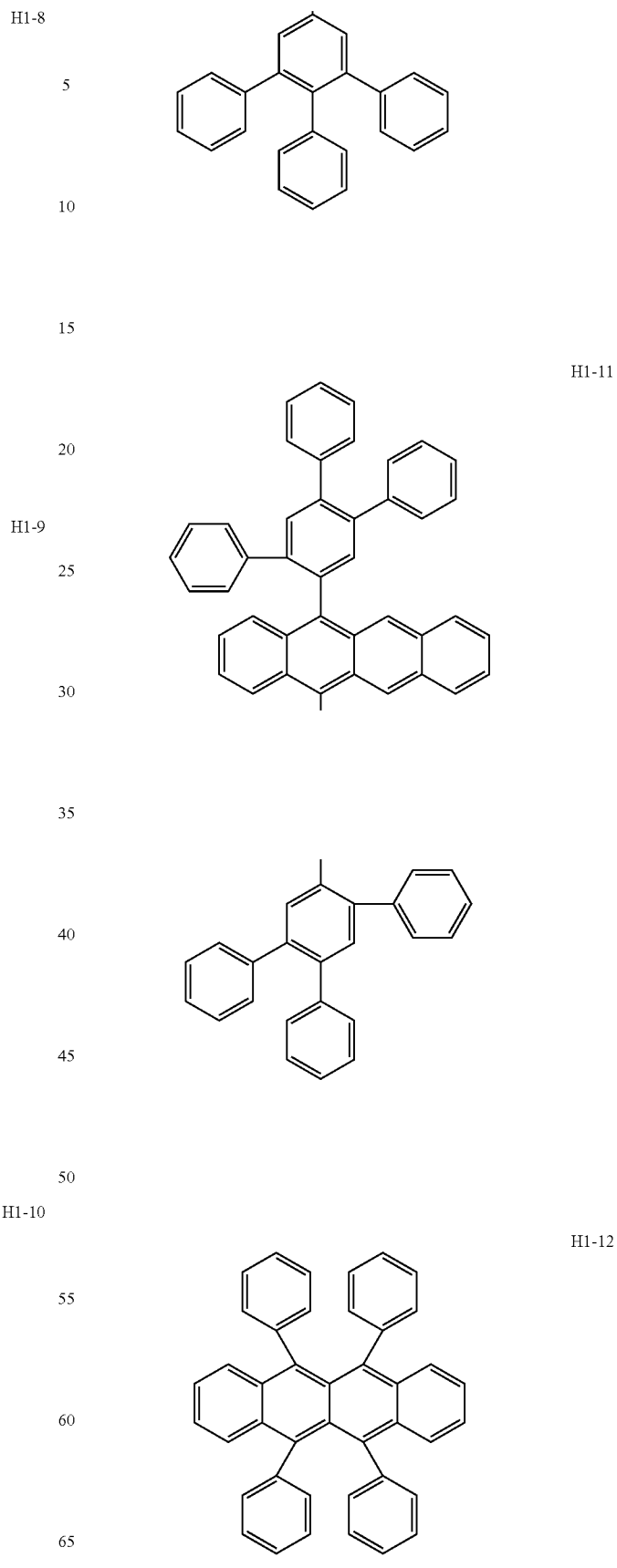

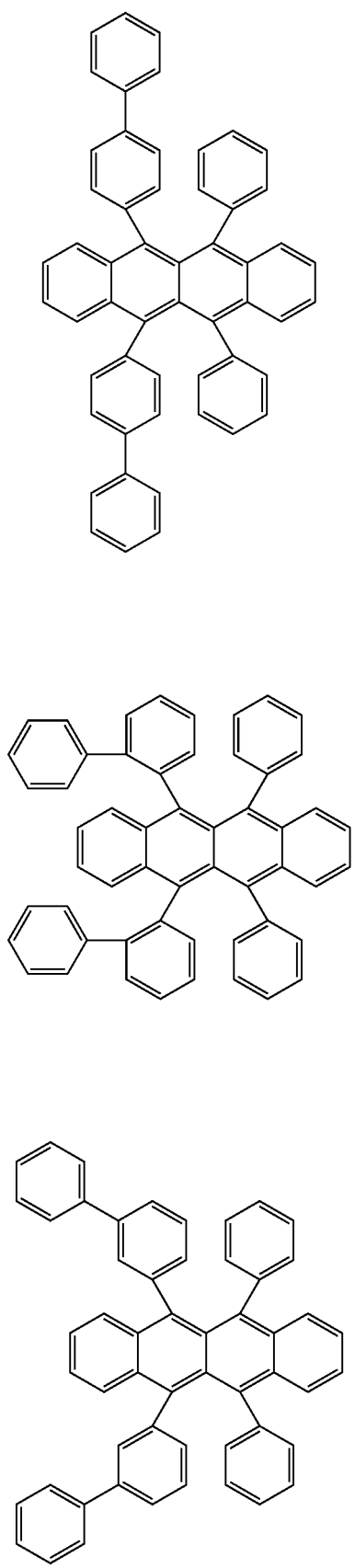
H1-13
H1-14
H1-15
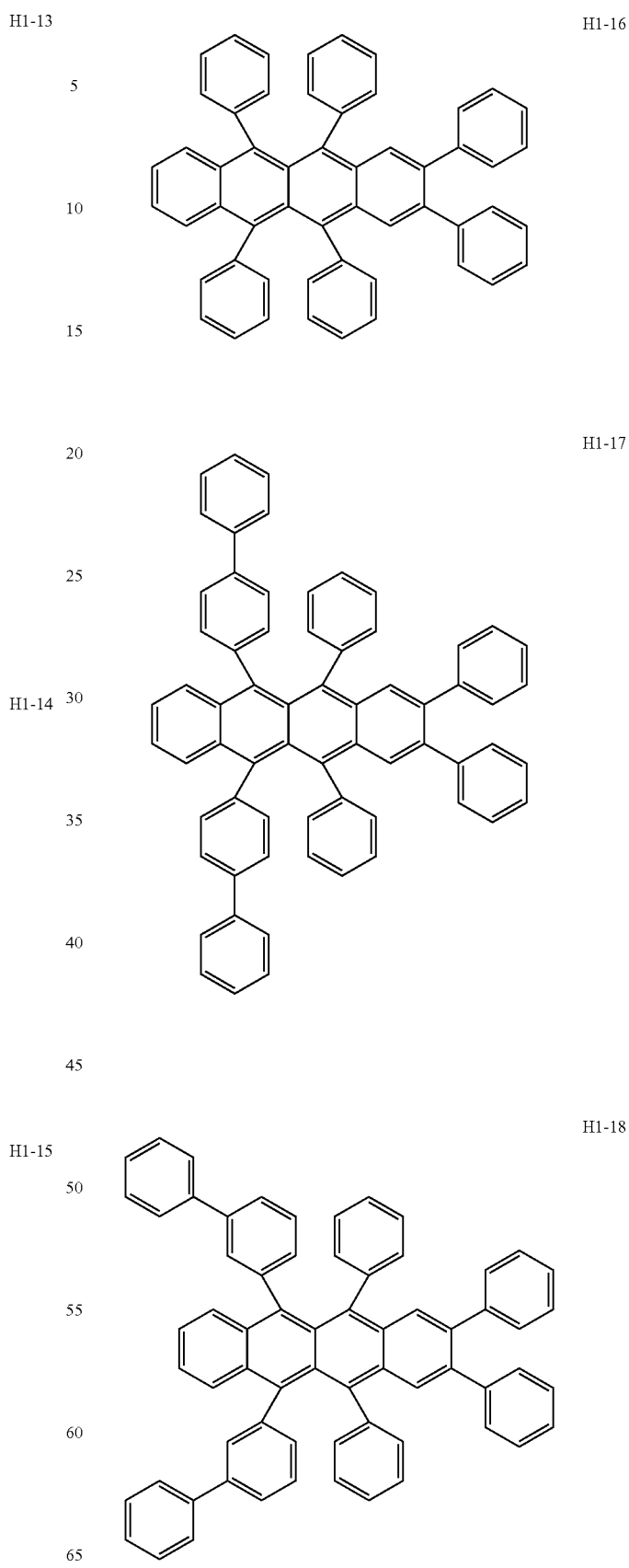
H1-16
H1-17
H1-18

H1-19
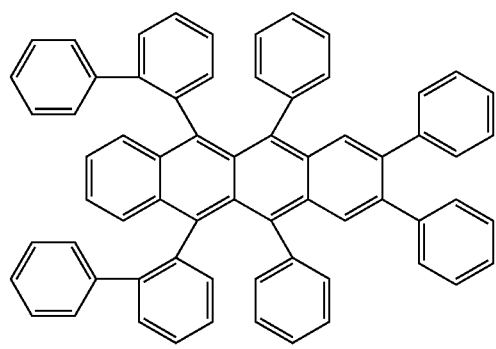
H1-20
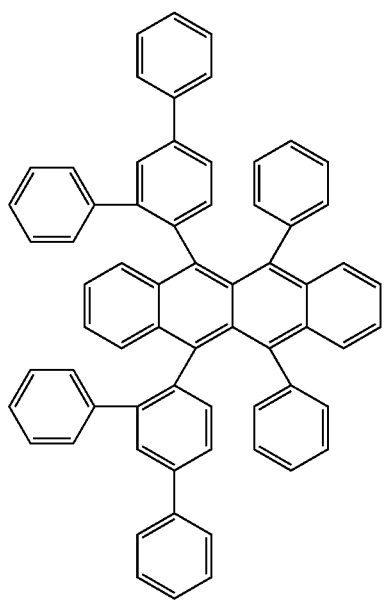
H1-21
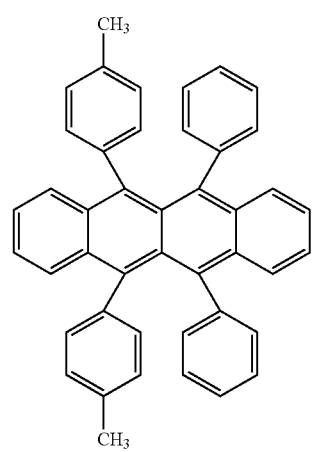
H1-22
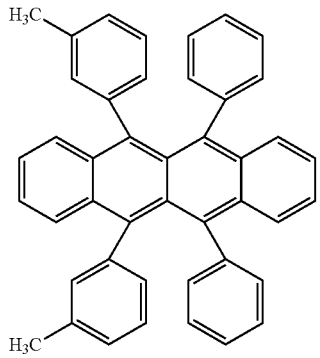
H1-23
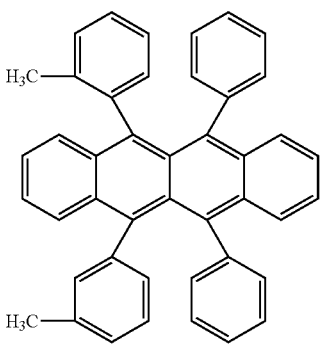
H1-24
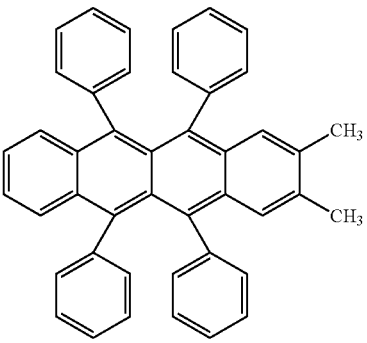
H1-25
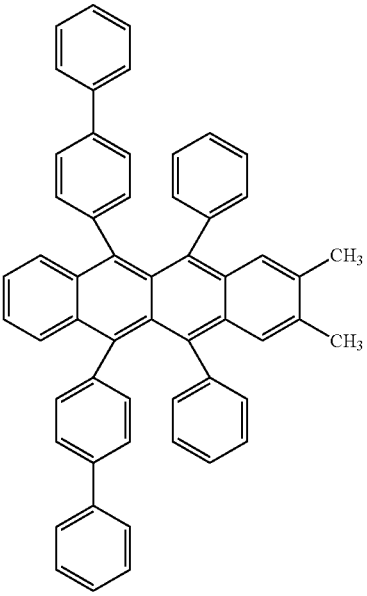

H1-26

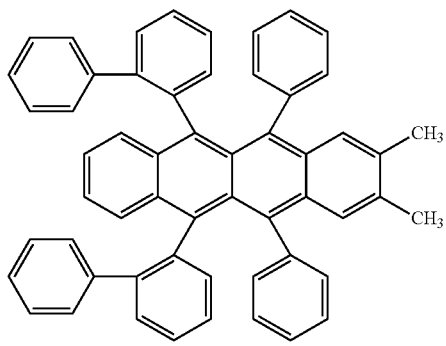

H1-27

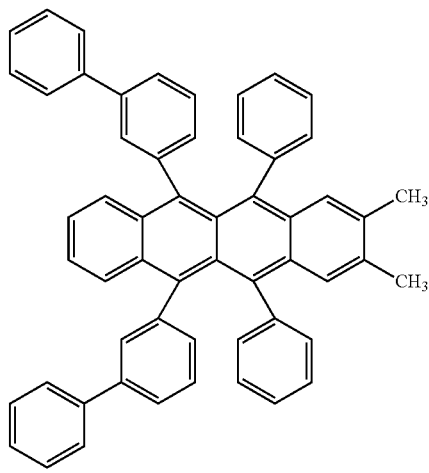

The content amount (doping amount) of the light emitting material within the light emitting layer 6 that includes such a light emitting material and the host material is preferably 0.01 to 10 wt %, and 0.1 to 5 wt % is more preferable. By setting the content amount of the light emitting material to such a range, the light emitting efficiency can be optimized.

Further, while the average thickness of the light emitting layer 6 is not particularly limited, approximately 1 to 60 nm is preferable, and approximately 3 to 50 nm is more preferable.

Electron Transport Layer

The electron transport layer 7 has a function of transporting the electrons that are injected from the cathode 9 via the electron injection layer 8 to the light emitting layer 6.

Examples of the constituent material (electron transportable material) of the electron transport layer 7 include a phenanthroline derivative such as 2,9-dimethyl-4,7-diphenyl-1,10-phenanthroline (BCP), an 8-quinolinol such as tris (8-quinolinolato)aluminum ($Alq_3$) or a quinoline derivative such as an organometallic complex in which the derivative thereof is the ligand, an azaindolizine derivative, an oxadiazole derivative, a perylene derivative, a pyridine derivative, a pyrimidine derivative, a quinoxaline derivative, a diphenoquinone derivative, a nitro-substituted fluorene derivative, and the like, and one or two or more types thereof may be used in combination.

Out of such materials, an azaindolizine derivative is preferably used as the electron transportable material that is used for the electron transport layer 7, and in particular, a compound that includes an azaindolizine skeleton and an anthracene skeleton within a molecule (hereinafter, simply referred to as an "azaindolizine-based compound") is more preferably used.

In such a manner, since a compound that includes an azaindolizine skeleton and an anthracene skeleton within a molecule is used as the electron transportable material of the electron transport layer 7 that is adjacent to the light emitting layer 6, electrons can be effectively transported from the electron transport layer 7 to the light emitting layer 6. The light emitting efficiency of the light emitting element 1 is therefore excellent.

Further, since the electron transport from the electron transport layer 7 to the light emitting layer 6 can be performed efficiently, the driving voltage of the light emitting element 1 can be lowered, and the life of the light emitting element 1 can accordingly be increased.

Furthermore, since a compound that includes an azaindolizine skeleton and an anthracene skeleton within a molecule has excellent stability (resistance) with respect to electrons and holes, the life of the light emitting element 1 can also be increased in such a regard.

It is preferable that the electron transportable material (azaindolizine-based compound) that is used as the electron transport layer 7 respectively have one or two of an azaindolizine skeleton and an anthracene skeleton within one molecule. In so doing, the electron transport layer 7 obtains excellent electron transportability and electron injectability.

Specifically, it is preferable that for example, the compounds represented by Formulae ELT-A1 to ELT-A24 below, the compounds represented by ELT-B1 to ELT-B12 below, and the compounds represented by ELT-C1 to ELT-C20 below be used as the azaindolizine-based compound that is used as the electron transport layer 7.

ETL-A1

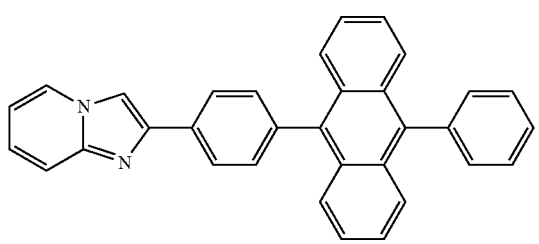

ETL-A2

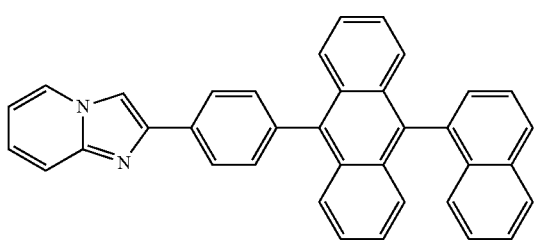

-continued
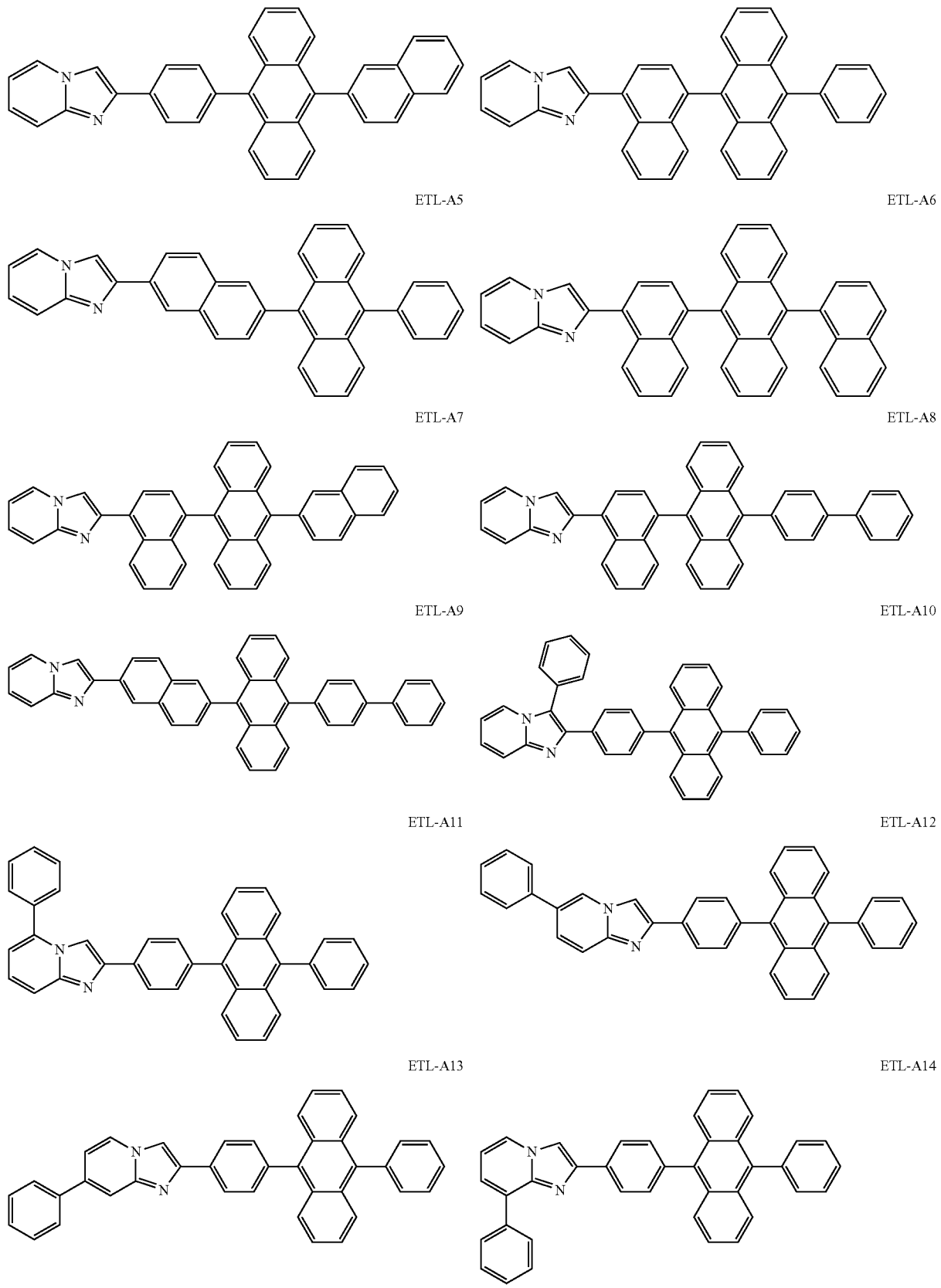

-continued
ETL-A-15
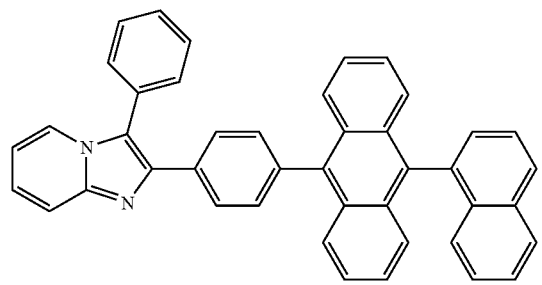
ETL-A16
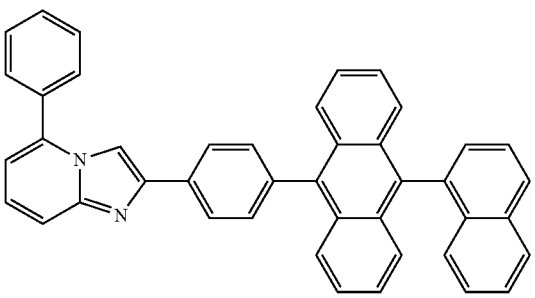
ETL-A17
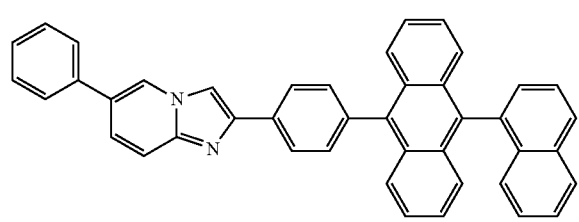
ETL-A18
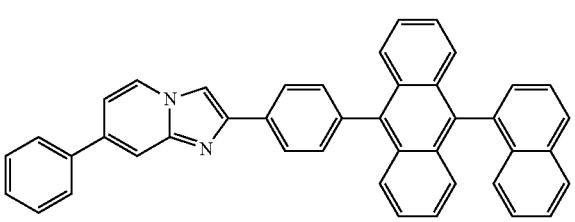
ETL-A19
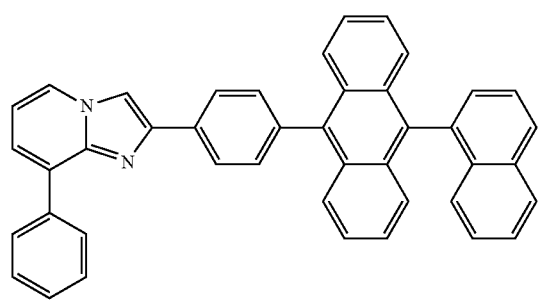
ETL-A20
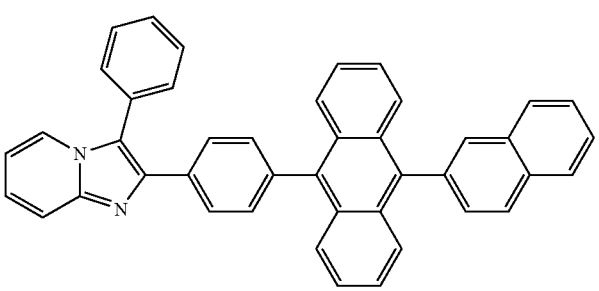
ETL-A21
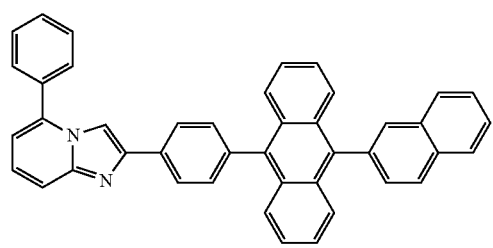
ETL-A22
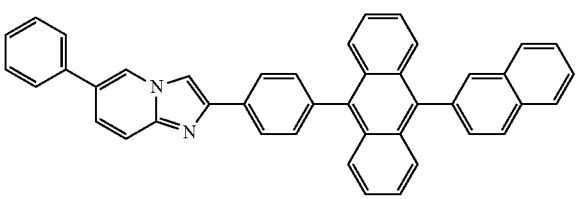
ETL-A23
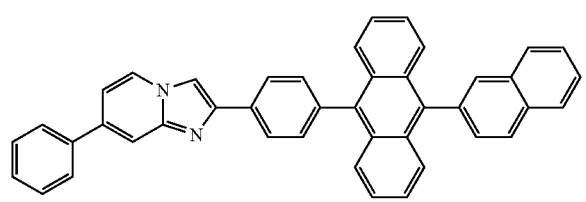
ETL-A24
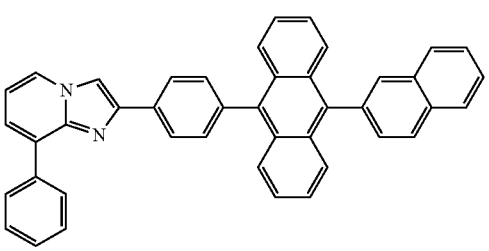

-continued
ETL-B1
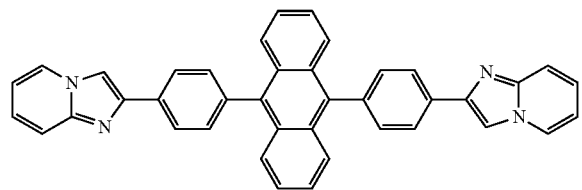
ETL-B2
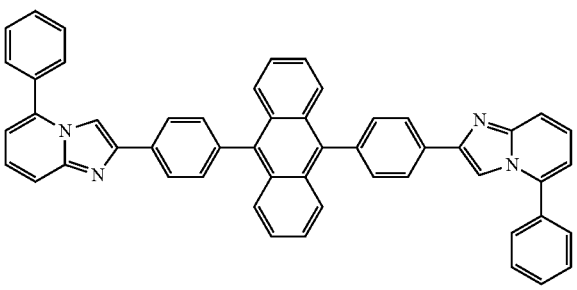
ETL-B3
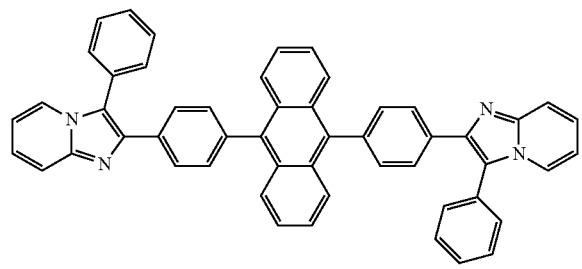
ETL-B4
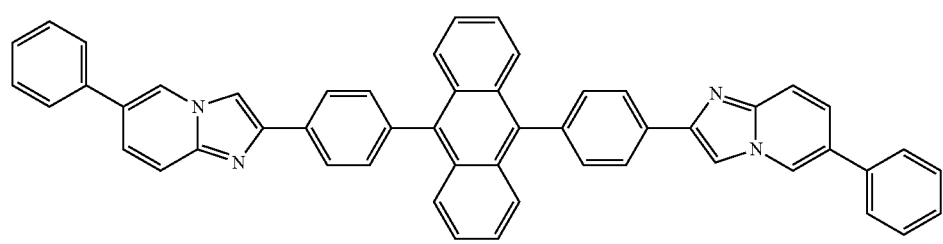
ETL-B5
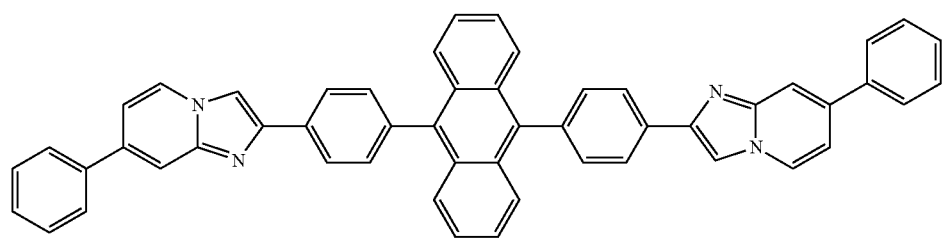
ETL-B6
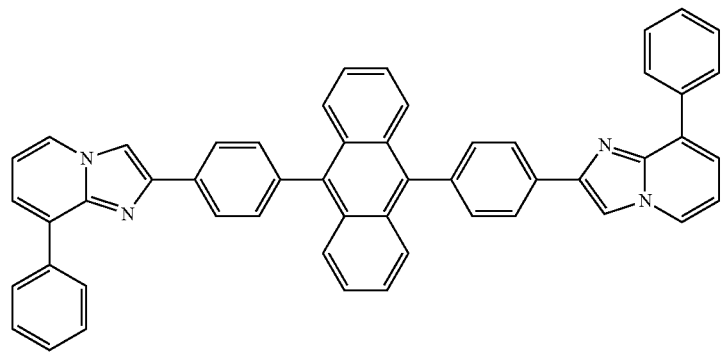

-continued
ETL-B7
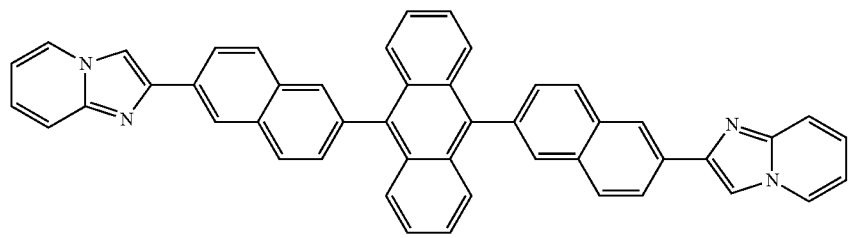
ETL-B8
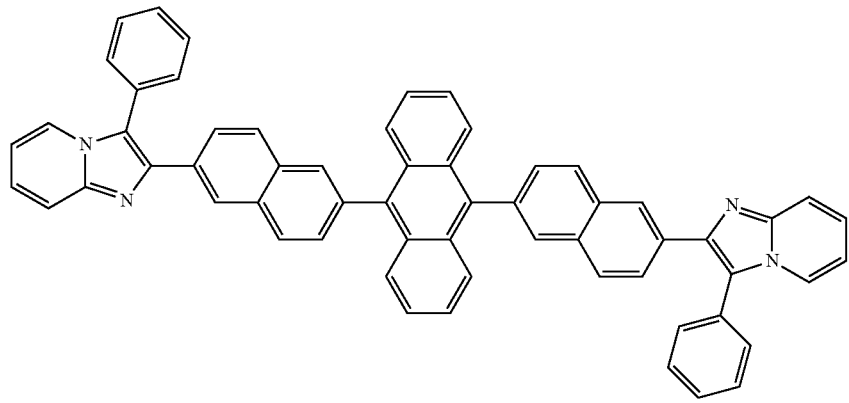
ETL-B9
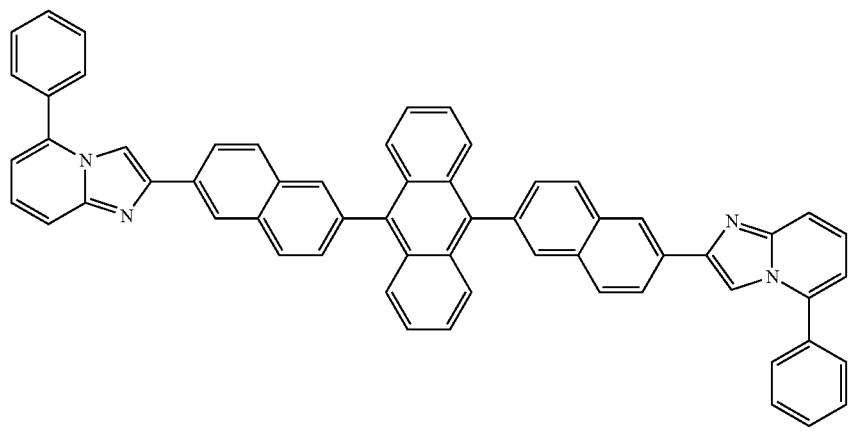
ETL-B10
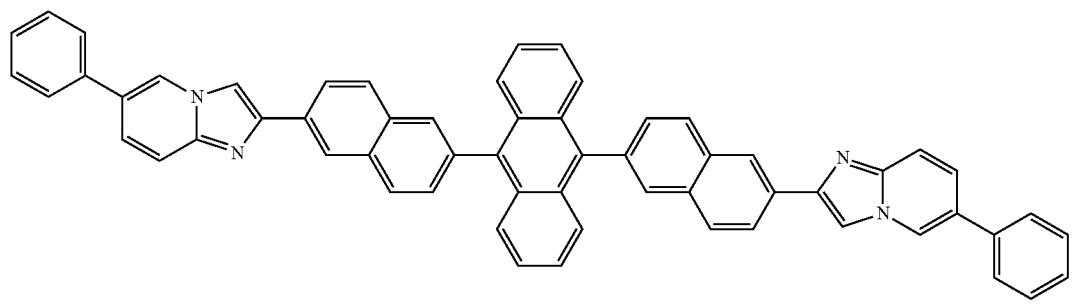
ETL-B11
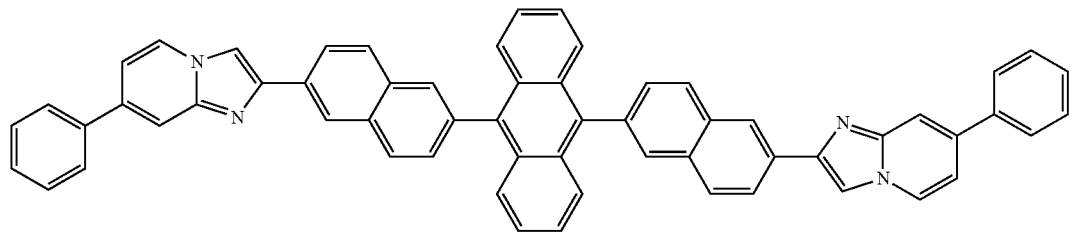

-continued
ETL-B12
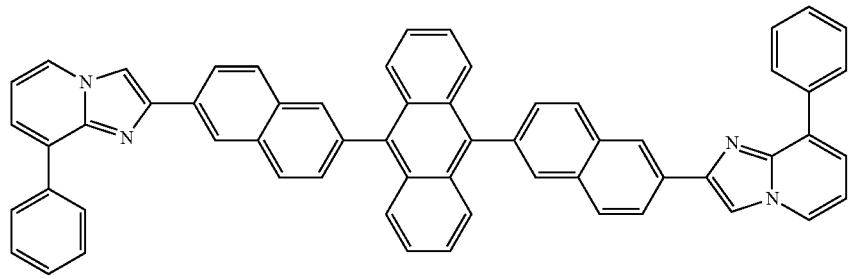
ETL-C1
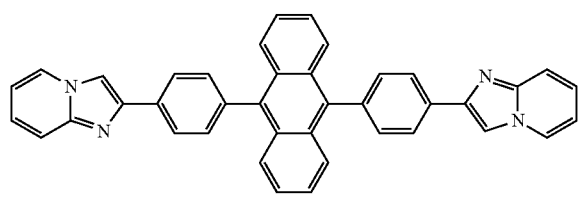
ETL-C2
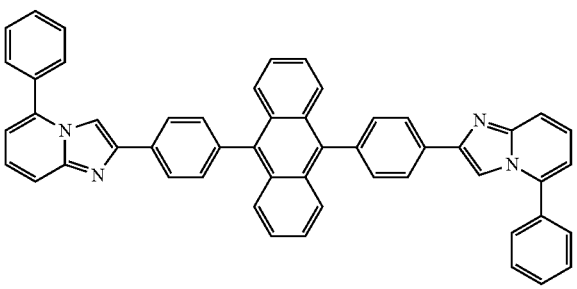
ETL-C3
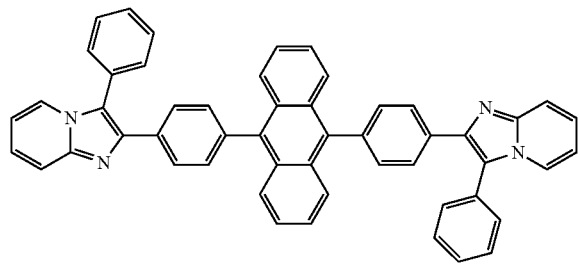
ETL-C4
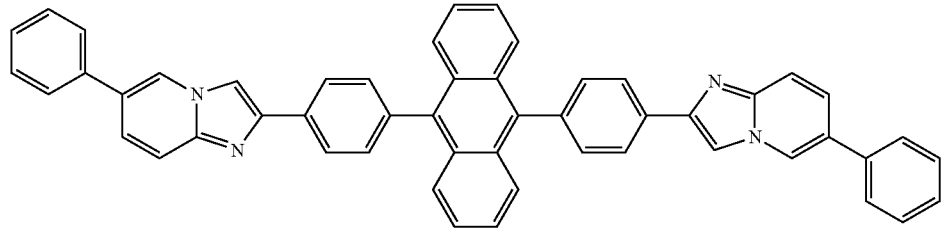
ETL-C5
ETL-C6
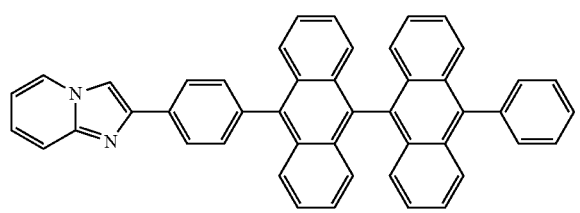
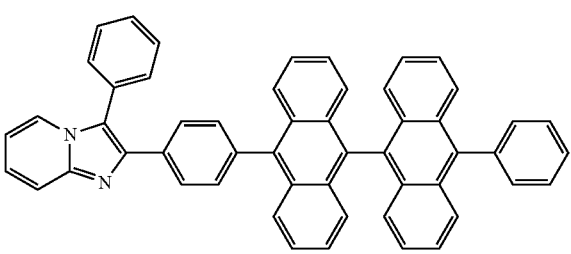
ETL-C7
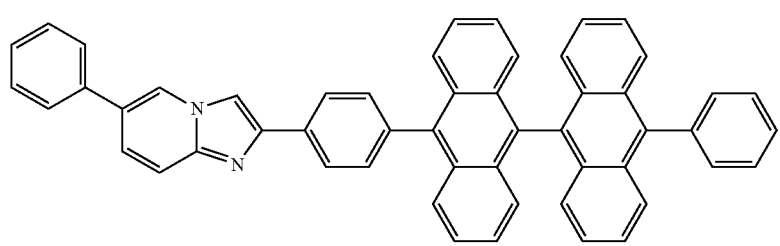

-continued
ETL-C8
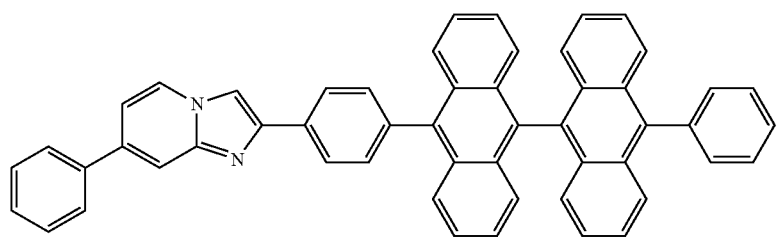
ETL-C9    ETL-C10
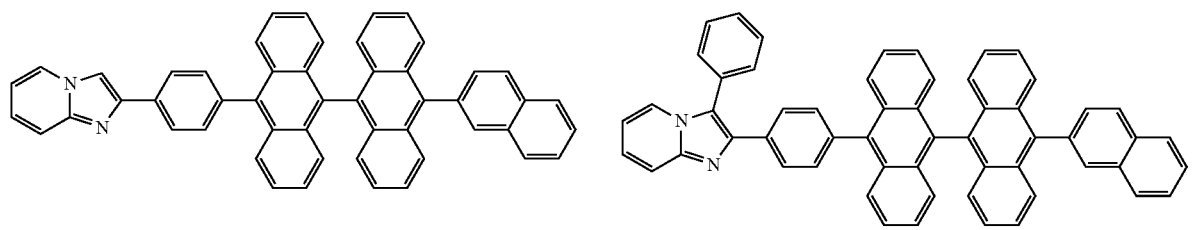
ETL-C11
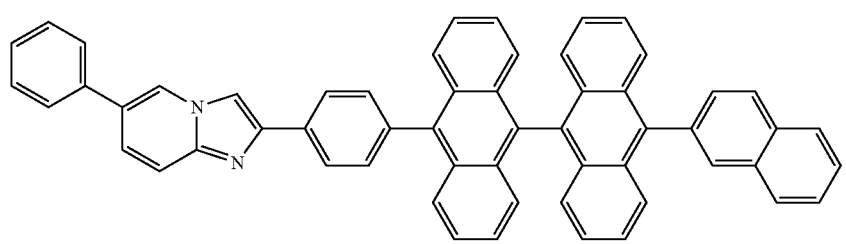
ETL-C12
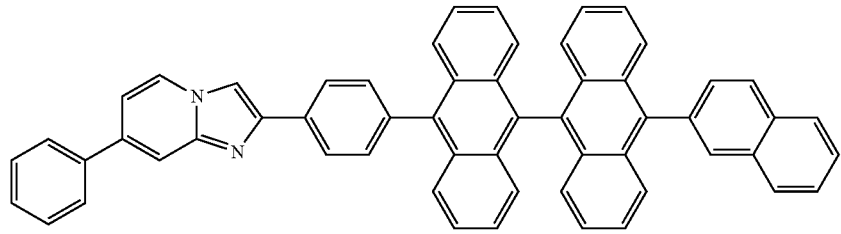
ETL-C13
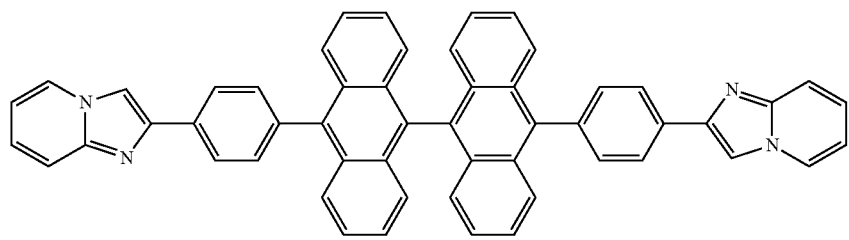
ETL-C14
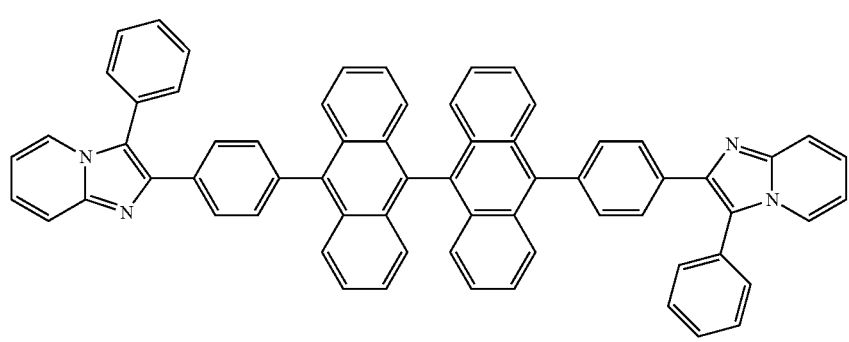

ETL-C15
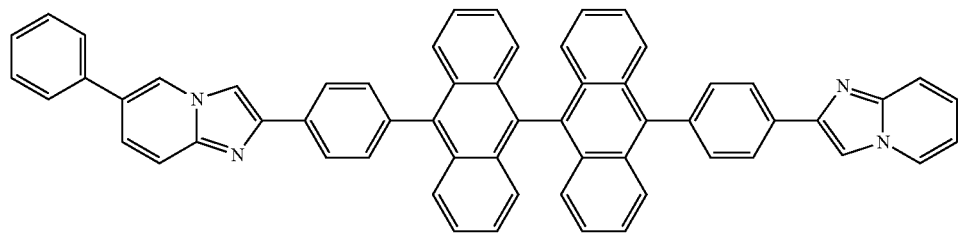
ETL-C16
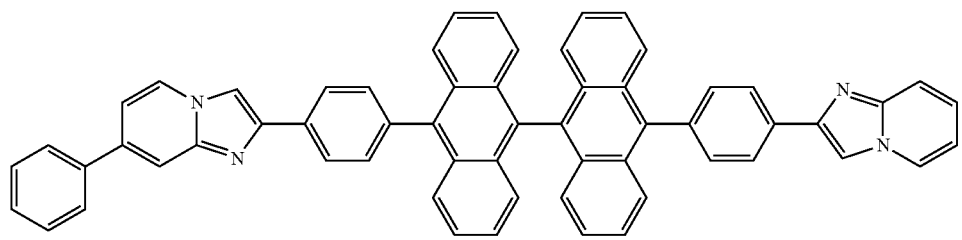
ETL-C17
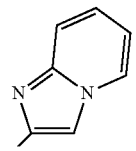
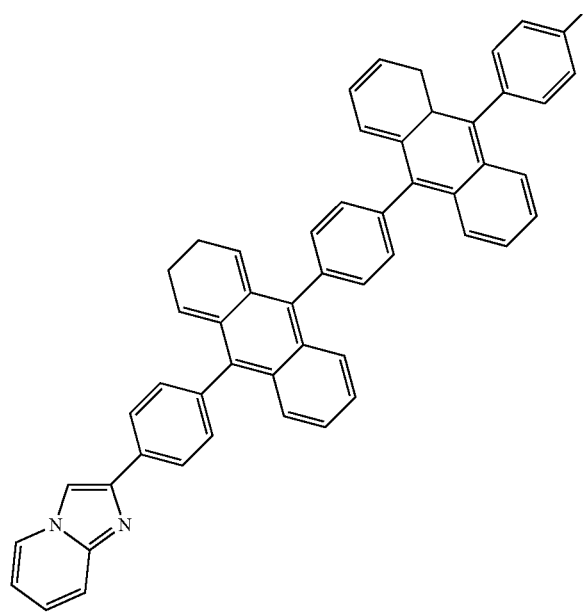
ETL-C18
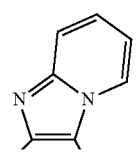

-continued
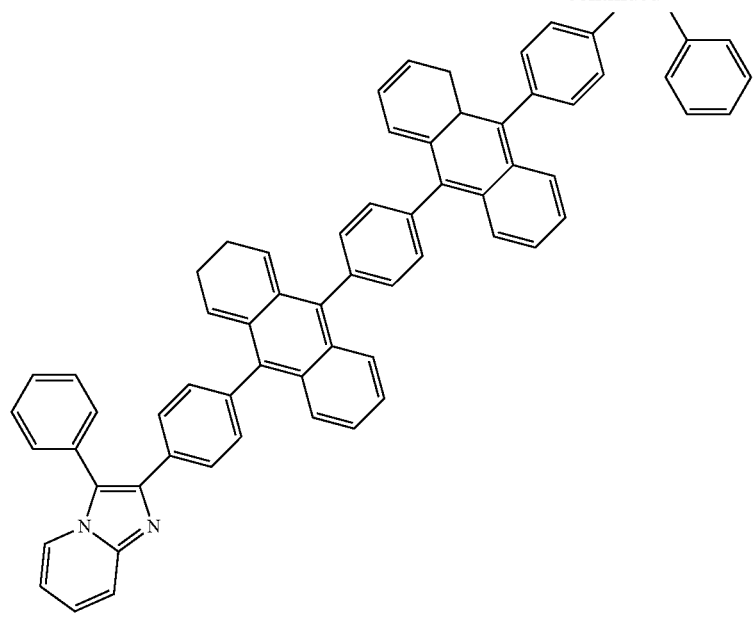
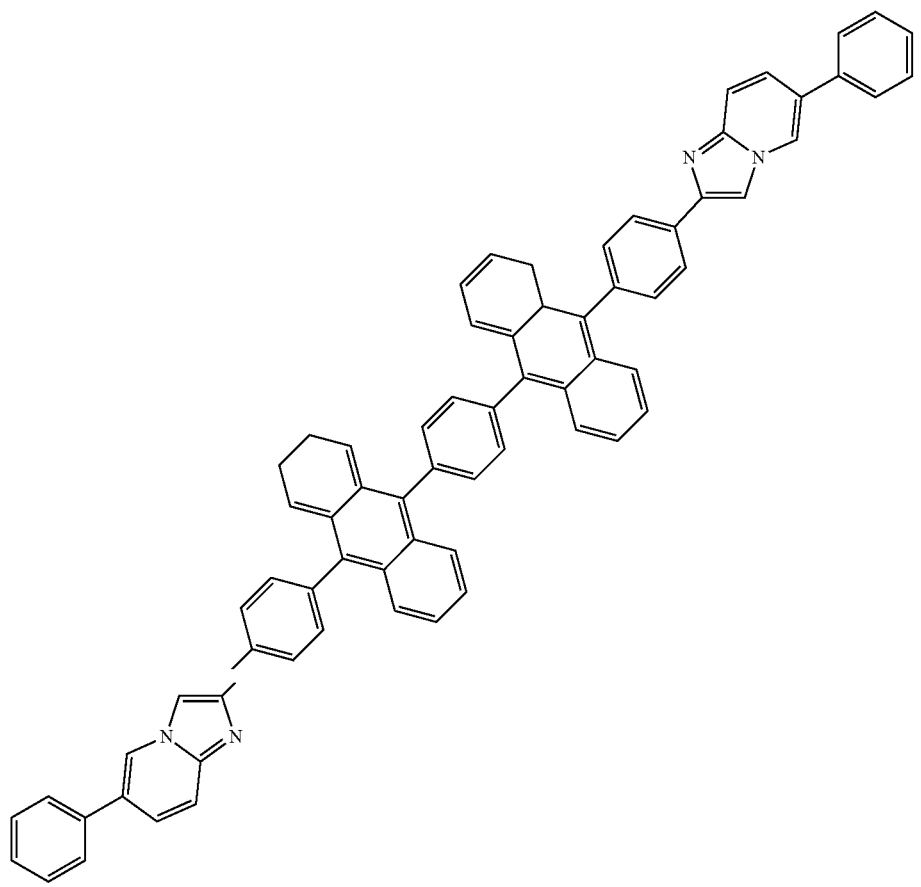
ETL-C19

-continued

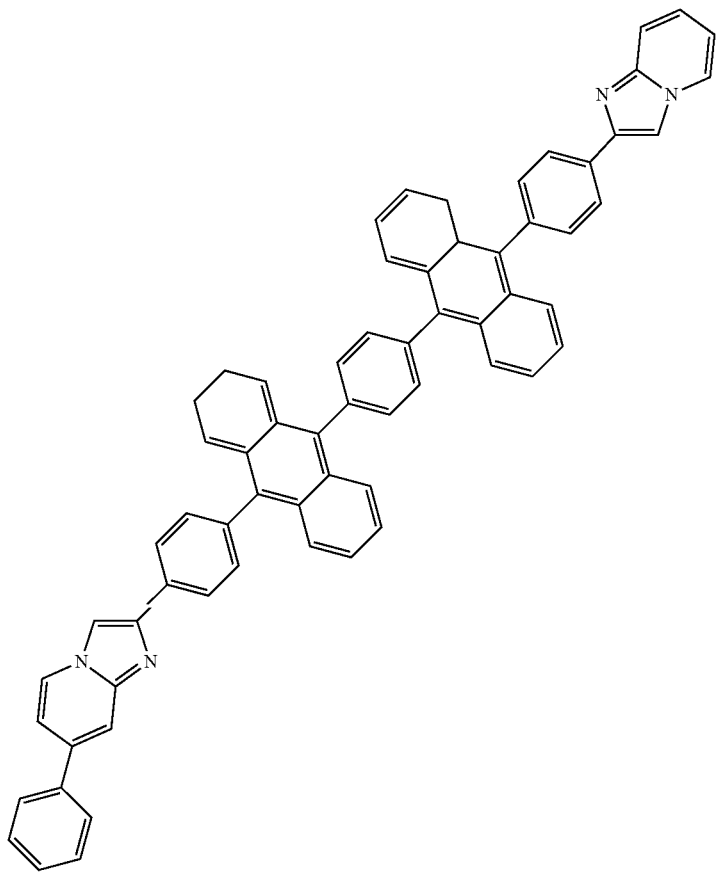

ETL-C20

Such an azaindolizine compound has excellent electron transportability and electron injectability. It is therefore possible to improve the light emitting efficiency of the light emitting element 1.

The reasons for the azaindolizine compound having excellent electron transportability and electron injectability are considered to be as below.

Since the entirety of the molecule of the azaindolizine-based compound described above that includes an azaindolizine skeleton and an anthracene skeleton within a molecule is connected by a π-conjugated system, the electron cloud is spread across the entirety of the molecule.

Furthermore, the portion of the azaindolizine skeleton of the azaindolizine-based compound has a function of receiving electrons and a function of sending the received electrons out to the portion of the anthracene skeleton. On the other hand, the portion of the anthracene skeleton of the azaindolizine-based compound has a function of receiving the electrons from the portion of the azaindolizine skeleton and a function of passing the received electrons over to the layer that is adjacent to the electron transport layer 7 on the anode 3 side, that is to the light emitting layer 6.

To describe specifically, the portion of the azaindolizine skeleton of the azaindolizine-based compound includes two nitrogen atoms, wherein one of the nitrogen atoms (on the side near the portion of the anthracene skeleton) has an sp2 hybrid orbital, and the other nitrogen atom (on the side far from the portion of the anthracene skeleton) has an sp3 hybrid orbital. Since the nitrogen atom with the sp2 hybrid orbital configures a portion of the conjugated system of the azaindolizine-based compound molecule, has a higher electronegativity than a carbon atom, and more strongly attracts electrons, the nitrogen atom functions as a portion that receives electrons. On the other hand, since the nitrogen atom with the sp3 hybrid orbital is not a normal conjugated system but has non-covalent electron pairs, the electrons of the nitrogen atom function as portions that send out electrons toward the conjugated system of the azaindolizine-based compound molecule.

On the other hand, since the portion of the anthracene skeleton of the azaindolizine-based compound is electrically neutral, such a portion can easily receive electrons from the portion of the azaindolizine skeleton. Further, since the portion of the anthracene skeleton of the azaindolizine-based compound has a large orbital overlap with the constituent material of the light emitting layer 6, particularly the host material (acene-based material), electrons can be easily passed over to the host material of the light emitting layer 6.

Further, since such an azaindolizine-based compound has excellent electron transportability and electron injectability as described above, as a result, the driving voltage of the light emitting element 1 can be decreased.

Further, the portion of the azaindolizine skeleton is stable even if the nitrogen atom with the sp2 hybrid orbital is reduced and even if the nitrogen atom with the sp3 hybrid orbital is oxidized. The azaindolizine-based compound therefore has high stability with respect to electrons and holes. As a result, the life of the light emitting element 1 can be increased.

Further, in a case when two or more types of the electron transportable materials described above are used in combination, the electron transport layer 7 may be configured by a mixed material in which two or more types of electron transportable materials are mixed, or may be configured by laminating a plurality of layers that are configured by different electron transportable materials.

While the average thickness of the electron transportable layer 7 is not particularly limited, approximately 1.0 to 200 nm is preferable, and approximately 10 to 100 nm is more preferable.

Electron Injection Layer

The electron injection layer 8 has a function of improving the electron injection efficiency from the cathode 9.

Examples of the constituent material of the electron injection layer 8 (electron injectable material) include various inorganic insulating materials and various inorganic semiconductor materials.

Examples of such organic insulating materials include alkali metal chalcogenides (oxides, sulfides, selenides, and tellurides), alkaline earth metal chalcogenides, halides of alkali metals, halides of alkaline earth metals, and the like, and one or two or more types thereof may be used in combination. By configuring the electron injection layer 8 with such materials as the principal material, the electron injectability can be improved. In particular, an alkali metal compound (alkali metal chalcogenides, halides of alkali metals, and the like) has an extremely small work function, and by configuring the electron injection layer 8 using an alkali metal compound, high brightness can be obtained for the light emitting element 1.

Examples of alkali metal chalcogenides include $Li_2O$, LiO, $Na_2S$, $Na_2Se$, NaO, and the like.

Examples of alkaline earth metal chalcogenides include CaO, BaO, SrO, BeO, BaS, MgO, CaSe, and the like.

Examples of alkali metal halides include CsF, LiF, NaF, KF, LiCl, KCl, NaCl, and the like.

Examples of alkaline earth metal halides include $CaF_2$, $BaF_2$, $SrF_2$, $MgF_2$, $BeF_2$, and the like.

Further, examples of inorganic semiconductor materials include an oxide, a nitride, a nitride oxide, or the like that includes at least one of the elements from Li, Na, Ba, Ca, Sr, Yb, Al, Ga, In, Cd, Mg, Si, Ta, Sb, and Zn, and one or two or more types thereof may be used in combination.

While the average thickness of the electron injection layer B is not particularly limited, approximately 0.1 to 1000 nm is preferable, approximately 0.2 to 100 nm is more preferable, and approximately 0.2 to 50 nm is still more preferable.

Here, the electron injection layer 8 may be omitted depending on the constituent materials, thicknesses, or the like of the cathode 9 and the electron transport layer 7.

Sealing Member

The sealing member 10 is provided to cover the anode 3, the laminated body 14, and the cathode 9, and has a function of sealing such portions in an airtight manner to block oxygen and moisture. By providing the sealing member 10, effects such as an improvement in the reliability of the light emitting element 1 and prevention of alteration and deterioration (improvement in resistance) can be obtained.

Examples of the constituent material of the sealing member 10 include Al, Au, Cr, Nb, Ta, Ti, or an alloy that includes such elements, silicon oxide, various resin materials, and the like. Here, in a case when a conductive material is used as the constituent material of the sealing member 10, it is preferable that an insulating film be provided between the sealing member 10 and the anode 3 and between the laminated body 14 and the cathode 9 as necessary in order to prevent short-circuiting.

Further, the sealing member 10 may be made to oppose the substrate 2 as a flat plate, and the gap between the sealing member 10 and the substrate 2 may be sealed by a sealing material such as, for example, a thermosetting resin.

According to the light emitting element 1 that is configured as described above, by using a thiadiazole-based compound as the light emitting material of the light emitting layer 6 and using a tetracene-based material as the host material of the light emitting layer 6, light emission at near-infrared bands is possible, and it is also possible to increase the efficiency and the life of the light emitting element 1.

The light emitting element 1 described above can be manufactured, for example, as below.

(1) First, the substrate 2 is prepared, and the anode 3 is formed on the substrate 2.

The anode 3 may be formed using, for example, a chemical vapor deposition method (CVD) such as plasma CVD or thermal CVD, a dry plating method such as vacuum deposition, a wet deposition method such as electrolytic plating, a thermal spraying method, a sol or gel method, an MOD method, joining of metallic foils, and the like.

(2) Next, the hole injection layer 4 is formed on the anode 3.

It is preferable that the hole injection layer 4 be formed by a gaseous phase process such as, for example, a CVD method, vacuum deposition, and a dry plating method such as sputtering.

Here, the hole injection layer 4 may also be formed, for example, by drying (reversing the dissolution or the dispersal) the hole injection layer formation material in which the hole injectable material is dissolved in a solvent or dispersed in a dispersal medium after supplying to the anode 3.

As the supply method of the hole injection layer formation material, for example, various application methods such as a spin coating method, a roll coating method, or an ink jet method may be used. By using such an application method, the hole injection layer 4 can be formed relatively easily.

Examples of the solution or the dispersal medium that is used in the preparation of the hole injection layer formation material include various inorganic solvents, various organic solvents, a mixed solvent including the above, or the like.

Here, drying may be performed, for example, by leaving the material in air or a depressurized atmosphere, by a heating process, by the blowing of an inert gas, or the like.

Further, an oxygen plasma process may be applied on the upper face of the anode 3 ahead of the present process. In so doing, it is possible to make the upper face of the anode 3 lyophilic, to remove (clean) the organic materials that are attached to the upper face of the anode 3, and to adjust the work function of the vicinity of the upper face of the anode 3.

Here, the conditions of the oxygen plasma process are, for example, preferably a plasma power of approximately 100 to 800 W, an oxygen gas flow rate of approximately 50 to 100 mL/min, a transfer speed of the processing target member (anode 3) of approximately 0.5 to 10 mm/sec, and a temperature of the substrate 2 of approximately 70 to 90° C.

(3) Next, the hole transport layer 5 is formed on the hole injection layer 4.

The light emitting layer 5 is preferably formed by a gaseous phase process using, for example, a dry plating method such as a CVD method, a vacuum deposition method, or sputtering.

Here, the hole transport layer 5 may also be formed, for example, by drying (reversing the dissolution or the dispersal)

the hole transportable material in which the hole transportable material is dissolved in a solvent or dispersed in a dispersal medium after supplying to the hole injection layer 4.

(4) Next, the light emitting layer 6 is formed on the hole transport layer 5.

The light emitting layer 6 may be formed by a gaseous phase process using a dry plating method such as, for example, vacuum deposition.

(5) Next, the electron transport layer 7 is formed on the light emitting layer 6.

It is preferable that the electron transport layer 7 be formed by a gaseous phase process using a dry plating method such as, for example vacuum deposition.

Here, the electron transport layer 7 may also be formed, for example, by drying (reversing the dissolution or the dispersal) the electron transport layer formation material in which the electron transportable material is dissolved in a solvent or dispersed in a dispersal medium after supplying to the light emitting layer 6.

(6) Next, the electron injection layer 8 is formed on the electron transport layer 7.

In a case when an inorganic material is used as the constituent material of the electron injection layer 8, the electron injection layer 8 may be formed, for example, using a gaseous phase process such as a dry plating method such as a CVD method, vacuum deposition, or sputtering, application and calcination of inorganic microparticle ink, or the like.

(7) Next, the cathode 9 is formed on the electron injection layer 8.

The cathode 9 may be formed using, for example, a vacuum deposition method, a sputtering method, joining of metallic foils, application and calcination of metallic microparticle ink, or the like.

The light emitting element 1 is obtained through the processes described above.

Finally, the sealing member 10 is placed over the obtained light emitting element 1 to cover the light emitting element 1, and the light emitting element 1 is joined to the substrate 2.

Light Emitting Device

Next, an aspect of the light emitting device of the invention will be described.

Figure 2:
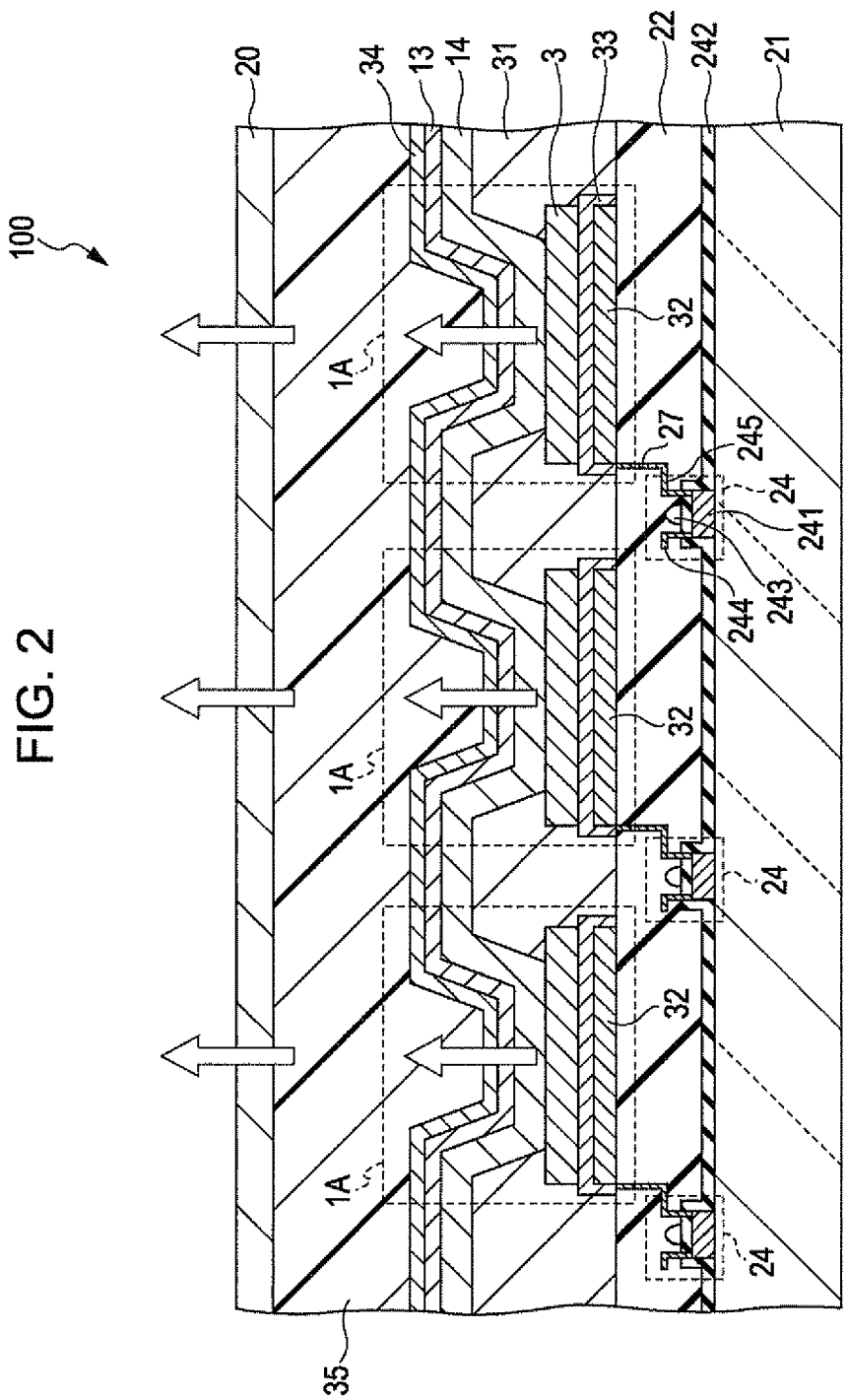
FIG. 2 is a longitudinal cross-sectional view that illustrates an aspect of a display device to which the light emitting device of the invention is applied.

FIG. 2 is a longitudinal cross-sectional view that illustrates an aspect of a display device to which the light emitting device of the invention is applied.

A display device 100 illustrated in FIG. 2 includes a substrate 21, a plurality of light emitting elements 1A and a plurality of driving transistors 24 for respectively driving each of the light emitting elements 1A. Here, the display device 100 is a display panel of a top emission structure.

The plurality of driving transistors 24 are provided on the substrate 21, and a flattening layer 22 that is configured by an insulating material is formed to cover the driving transistors 24.

Each driving transistor 24 includes a semiconductor layer 241 made of silicon, a gate insulating layer 242 that is formed on the semiconductor layer 241, a gate electrode 243 that is formed on the gate insulating layer 242, a source electrode 244, and a drain electrode 245.

The light emitting elements 1A are provided on the flattening layer to correspond to each of the driving transistors 24.

With the light emitting elements 1A, a reflective film 32, a corrosion prevention film 33, the anode 3, the laminated body (organic EL light emitting unit) 14, a cathode 13, and a cathode cover 34 are laminated in such an order on the flattening layer 22. According to the present aspect, the anode 3 of each light emitting element 1A configures a pixel electrode, and is electrically connected to the drain electrode 245 of each driving transistor 24 by a conductive unit (wiring) 27. Further, the cathode 13 of each light emitting element 1A is a common electrode.

The light emitting elements 1A of FIG. 2 emit light at near-infrared bands.

A bulkhead 31 is provided between adjacent light emitting elements 1A. Further, an epoxy layer 35 that is configured by an epoxy resin is formed on the light emitting elements 1A to cover such portions.

Furthermore, a sealing substrate 20 is provided on the epoxy layer 35 to cover such portions.

The display device 100 described above may be used, for example, as a near-infrared display for military applications and the like.

According to such a display device 100, light emission at near-infrared bands is possible. Further, since the display device 100 includes light emitting elements 1A with high efficiency and long life, the display device 100 has excellent reliability.

Authentication Device

Next, an aspect of the authentication of the invention will be described.

Figure 3:
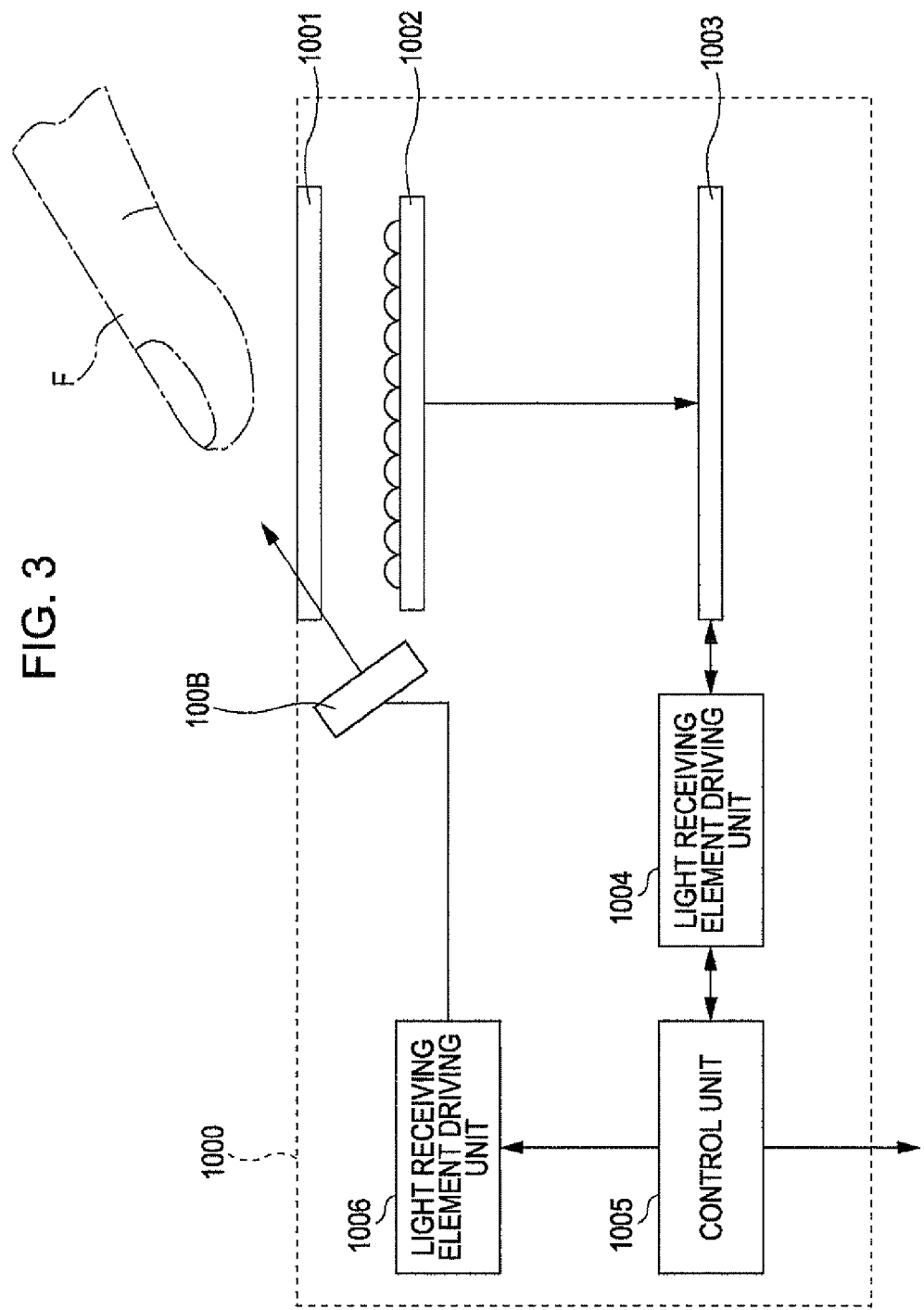
FIG. 3 is a diagram that illustrates an aspect of the authentication device of the invention.

FIG. 3 is a diagram that illustrates the aspect of the authentication device of the invention.

An authentication device 1000 illustrated in FIG. 3 is a biometric authentication device that authenticates individuals using biometric information of a living body F (a fingertip in the present aspect).

The authentication device 1000 includes a light source 100B, a cover glass 1001, a micro lens array 1002, a light receiving element group 1003, a light emitting element driving unit 1006, a light receiving element driving unit 1004, and a control unit 1005.

The light source 100B includes a plurality of the light emitting elements 1 described above, and irradiates near-infrared light toward the living body F that is the imaging target. For example, the plurality of light emitting elements 1 of the light source 100B are arranged along the outer circumference portion of the cover glass 1001.

The cover glass 1001 is a portion that is in contact with or in the vicinity of the living body F.

The micro lens array 1002 is provided on the opposite side to the side of the cover glass 1001 which is in contact with or in the vicinity of the living body F. The micro lens array 1002 is configured by arranging a plurality of micro lenses in a matrix pattern.

The light receiving element group 1003 is provided on the opposite side to the cover glass 1001 with respect to the micro lens array 1002. The light receiving element group 1003 is configured by a plurality of light receiving elements that are provided in a matrix pattern corresponding to the plurality of micro lenses of the micro lens array 1002. As each of the light receiving elements of the light receiving element group 1003, for example, a CCD (Charge Coupled Device), a CMOS, or the like may be used.

The light emitting element driving unit 1006 is a driving circuit that drives the light source 100B.

The light receiving element driving unit 1004 is a driving circuit that drives the light receiving element group 1003.

The control unit 1005 is an MPU, for example, and has a function of controlling the driving of the light emitting element driving unit 1006 and the light receiving element driving unit 1004.

Further, the control unit 1005 has a function of performing authentication of the living body F by a comparison of the light receiving results of the light receiving element group 1003 and biometric authentication information that is stored in advance.

For example, the control unit 1005 generates an image pattern (for example, a vein pattern) relating to the living body F based on the light receiving results of the light receiving element group 1003. Furthermore, the control unit 1005 compares such an image pattern with an image pattern that is stored in advance as biometric authentication information, and performs authentication (for example, vein authentication) of the living body F based on the comparison result.

According to such an authentication device 1000, biometric authentication can be performed using near-infrared light. Further, since the authentication device 1000 includes the light emitting element 1 with high efficiency and long life, the authentication device 1000 has excellent reliability.

Such an authentication device 1000 can be built into various electronic apparatuses.

Electronic Apparatus

Figure 4:
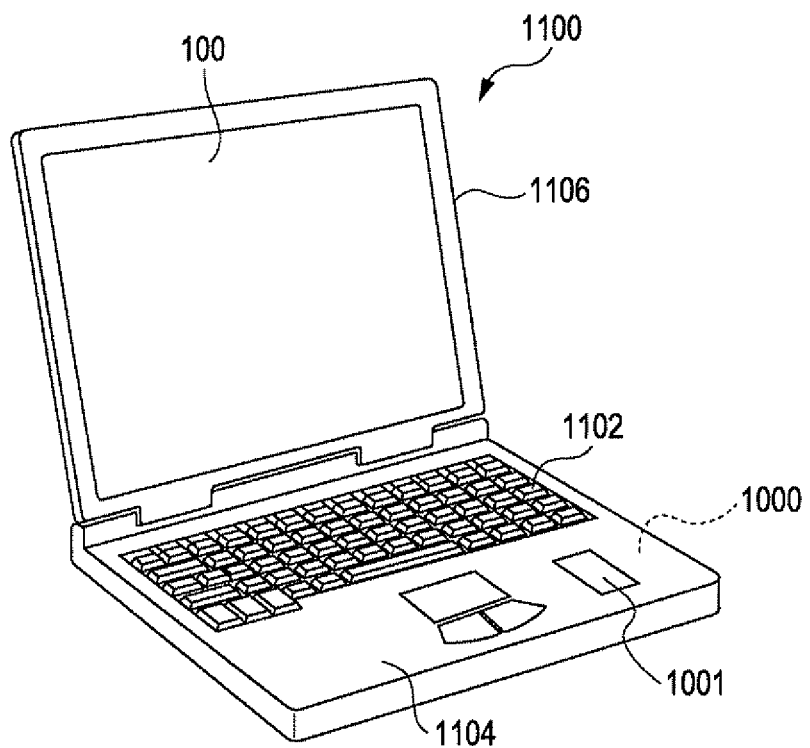
FIG. 4 is a perspective diagram that illustrates the configuration of a mobile (or notebook) personal computer to which the electronic apparatus of the invention is applied.

FIG. 4 is a perspective diagram that illustrates the configuration of a mobile (or notebook) personal computer to which the electronic apparatus of the invention is applied.

In the drawing, a personal computer 1100 is configured by a main body portion 1104 that includes a keyboard 1102 and a display unit 1106 that includes a display portion, and the display unit 1106 is supported to be rotatable via a hinge structure portion with respect to the main body portion 1104.

With the personal computer 1100, the authentication device 1000 described above is provided on the main body portion 1104.

Since such a personal computer 1100 includes the light emitting element 1 with high efficiency and long life, the personal computer 1100 has excellent reliability.

Here, other than the personal computer (mobile personal computer) of FIG. 4, the electronic apparatus of the invention can be applied, for example, to a mobile phone, a digital still camera, a television, a video camera, a viewfinder type or monitor direct view type video tape recorder, a laptop personal computer, a car navigation device, a pager, an electronic diary (also including those with a communication function), an electronic dictionary, a calculator, an electronic game console, a word processor, a work station, a television phone, security television monitor, electronic binocular, a POS terminal, an apparatus that includes a touch panel (for example, a cash dispenser of a financial institution, a vending machine), a medical apparatus (for example, an electronic thermometer, a blood pressure meter, a blood sugar meter, a pulse measurement device, a pulse wave measurement device, an electrocardiographic display device, an ultrasonic diagnostic device, an endoscope display device), a fish finder, various measurement apparatuses, meters (for examples, meters for rolling stock, aircraft, and ships), a flight simulator, various other monitors, and a projection type display device such as a projector.

While the thiadiazole-based compound, the light emitting element compound, the light emitting element, the light emitting device, the authentication device, and the electronic apparatus of the invention have been described above based on the aspects shown in the drawings, the invention is not limited thereto.

For example, the light emitting element and the light emitting device of the invention may be used as a light source for illumination.

EXAMPLES

Next, specific examples of the invention will be described.

1. Manufacture of Thiadiazole-Based Compound

Synthesis Example A1

Synthesis of Compound Represented by Formula D-1

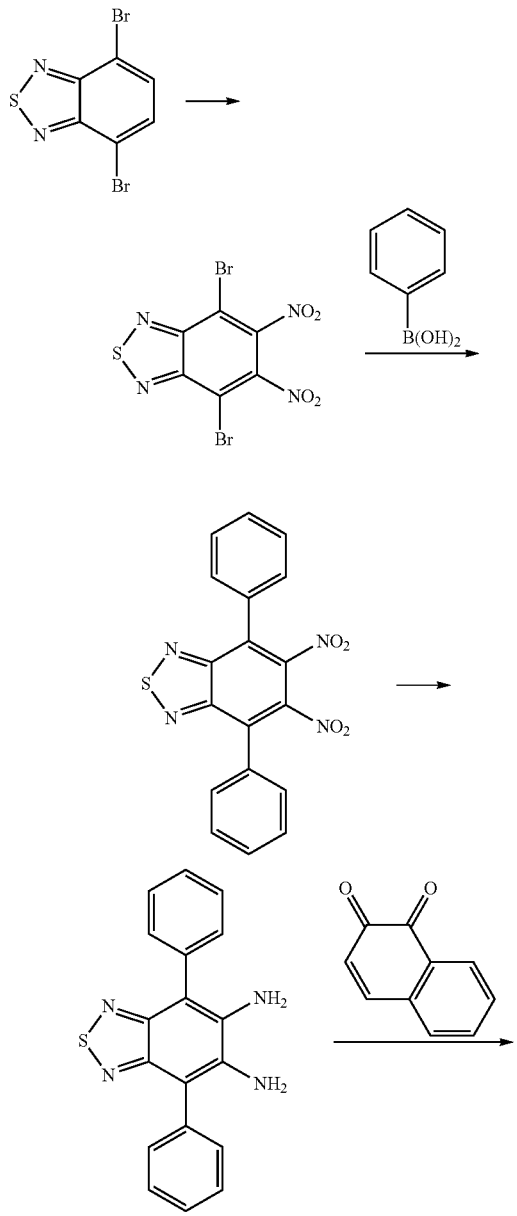

-continued

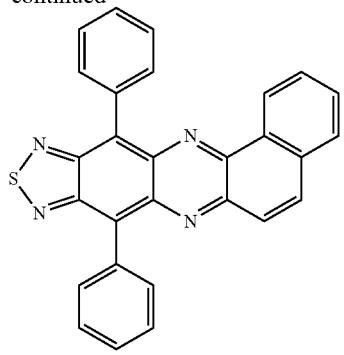

Synthesis A1-1

1500 ml of fuming nitric acid was poured into a 5-liter flask and cooled. 1500 ml of sulfuric acid was then added in portions while maintaining the temperature between 10 and 50° C. 150 g of Compound a that is dibromo-benzothiadiazole of the original material was then slowly added over the course of one hour. The temperature of the solution at this point was kept to be equal to or lower than 5° C. When the entire amount was added, the mixture was reacted for 20 hours at room temperature (25° C.) After the reaction, the reaction solution was poured on 3 kg of ice and stirred overnight. The mixture was then filtered and washed with methanol and heptane.

After heating and dissolving the filtered residue with 200 ml of toluene, the material was slowly cooled to room temperature and filtered, and the residue was cooled with a small amount of toluene and dried under reduced pressure.

In so doing, 60 g of Compound b (4,7-dibromo-5,6-dinitro-benzo[1,2,5]thiadiazole) with an HPLC purity of 950 was obtained.

Synthesis A1-2

30 g of Compound b that is the obtained dibromo compound, 23 g of phenylboronic acid (commercially available product), 2500 ml of toluene, and 2M cesium carbonate aqueous solution (152 g/(distilled water) 234 ml) were poured into a 5-liter flask in an atmosphere of Ar and reacted overnight at 90° C. After reacting, the mixture was filtered, separated, and concentrated, and the 52 g of the obtained coarse substance was separated by a silica gel column (5 kg of $SiO_2$) to obtain a magenta solid substance.

In so doing, 6 g of Compound c (5,6-dinitro-4,7-diphenyl-benzo[1,2,5]thiadiazole) with an HPLC purity of 96% was obtained.

Synthesis A1-3

6 g of Compound c that is the obtained dinitro compound, 7 g of reduced iron, and 600 ml of acetic acid were poured into a 1-liter flask in an atmosphere of Ar and cooled to room temperature after reacting at 80° C. for four hours. After reacting, the reaction solution was poured into 1.5 l of deionized water, and 1.5 l of ethyl acetate was added thereto. After the addition, since a solid substance was separated, 1 l of tetrahydrofuran and 300 g of salt were added and separated as liquids. The aqueous layer was re-extracted by the 1 l of tetrahydrofuran. After concentrating and drying, the material was washed once again by a small amount of water an ethanol to obtain an orange solid substance.

In so doing, 7 g of Compound d (4,7-diphenyl-benzo[1,2,5]thiadiazole-5,6-diamine) with an HPLC purity of 80% was obtained.

Synthesis A1-4

4.5 g of Compound d that is the obtained diamine compound, 2.2 g of 1,2-naphthoquinone, and 300 ml of acetic acid as a solvent were poured into a 1-liter flask in an atmosphere of Ar and reacted at 80° C. for two hours. After reacting, the reaction liquid was cooled to room temperature, poured into 1 l of deionized water, and the crystals were filtered and washed to obtain 7 g of black solid substance. Furthermore, the black solid substance was purified with a silica gel column (1 kg of $SiO_2$).

In so doing, 4.5 g of Compound e (compound represented by Formula D-1 above) with an HPLC purity of 99% was obtained. When Compound e was mass analyzed, Compound e was M+:440.

Furthermore, the obtained Compound e was purified by sublimation at a set temperature of 340° C. Compound e after the purification by sublimation had an HPLC purity of 99%.

Synthesis Example A2

Synthesis of Compound Represented by Formula D-2

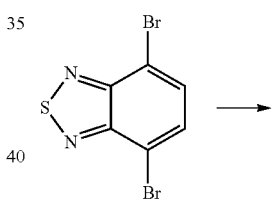

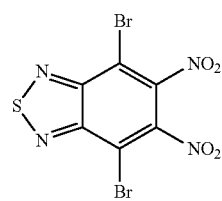

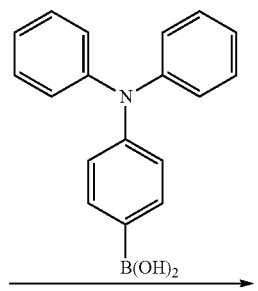

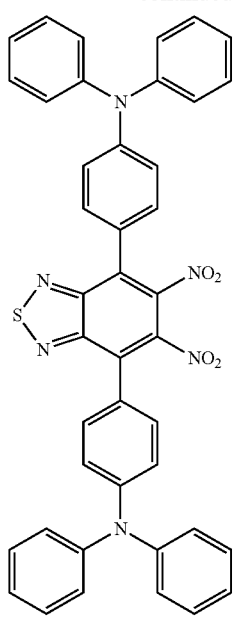

→

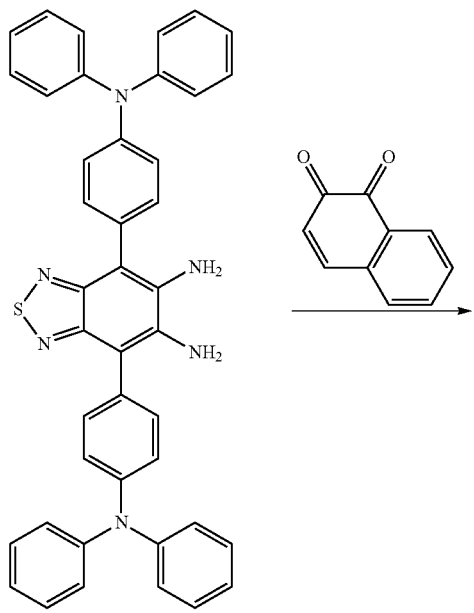

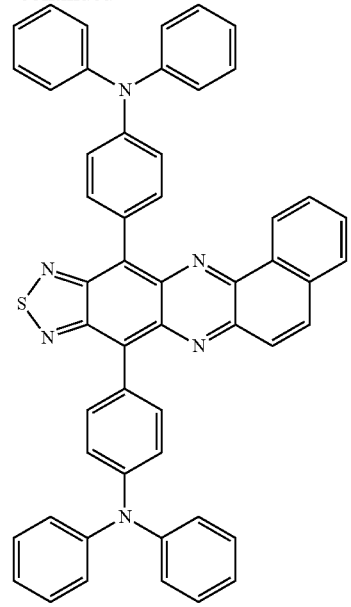

Synthesis was performed similarly to Synthesis Example A1 described above except that the boronic acid substance of triphenylamine was used instead of the phenylboronic acid used in Synthesis A1-2 in Synthesis Example A1 described above. In so doing, Compound h represented by Formula D-2 above was obtained.

Here, during the synthesis of the boronic acid substance of triphenylamine, 246 g of 4-bromo-triphenylamine (commercially available product) and 1500 ml of dehydrated tetrahydrofuran were poured into a 5-liter flask in an atmosphere of Ar, and 570 ml of 1.6M n-BuLi/hexane solution was added dropwise over three hours at −60° C. Thirty minutes later, 429 g of triisopropyl borate was added dropwise over one hour. After the dropwise addition, the mixture was reacted at the resulting temperature overnight. After the reaction, 2 l of water was added dropwise, after which the mixture was extracted and separated with 2 l of toluene. The organic layer was concentrated, recrystallized, filtered, and dried to obtain 160 g of the desired white boronic acid substance.

The HPLC purity of the obtained boronic acid substance was 99%.

Furthermore, Compound f was obtained by performing the same synthesis as Synthesis A1-2 of Synthesis Example A1 described above using the obtained boronic acid substance.

Using the obtained Compound f, the same synthesis as Synthesis A1-3 of Synthesis Example A1 described above was performed to obtain Compound g.

Compound h represented by Formula D-2 above was obtained by performing the same synthesis as Synthesis A1-4 of Synthesis Example A1 described above using the obtained Compound h.

In so doing, 3 g of Compound h (compound represented by Formula D-2 described above) with an HPLC purity of 99% which is a dark blue solid substance in external appearance was obtained. When Compound h was mass analyzed, Compound h was M+:774.

Furthermore, the obtained Compound h was purified by sublimation at a set temperature of 360° C. Compound h after the purification by sublimation had an HPLC purity of 99%.

Synthesis Example A3

Synthesis of Compound Represented by Formula D-3

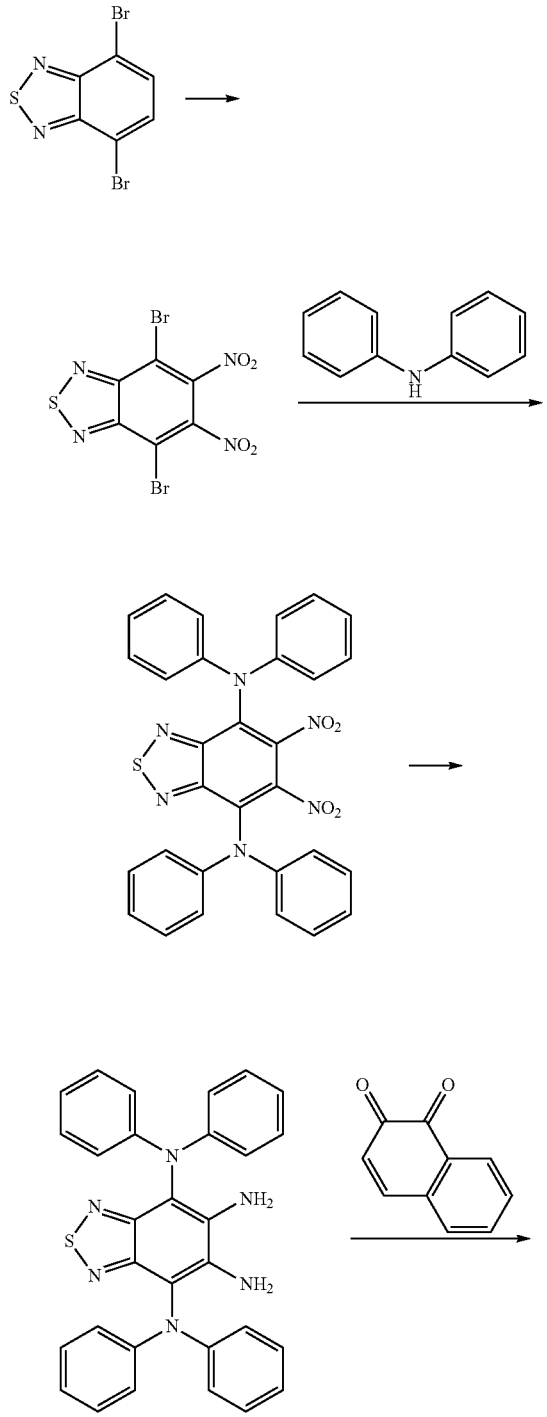

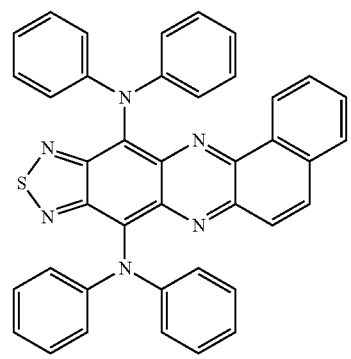

Synthesis was performed similarly to Synthesis Example A1 described above except that diphenylamine was used instead of the phenylboronic acid used in Synthesis A1-2 in Synthesis Example A1 described above. In so doing, Compound k represented by Formula D-3 above.

Here, during the synthesis using diphenylamine, 11 g of tetrakistriphenylphosphine Pd(0) was dissolved in 100 ml of toluene in a 300 ml flask and heated to 100° C. in an atmosphere of Ar. 8 g of tri-t-butylphosphine was then added to the mixture and reacted for 30 minutes to create a catalyst (Pd catalyst).

Meanwhile, 30 g of Compound b that is a dibromo substance and 33 g of diphenylamine (commercially available product) were dissolved in 2500 ml of toluene and heated to 100° C. in a 5-liter flask in an atmosphere of Ar. The Pd catalyst prepared in advance and 20 g of t-BuOK were then added and overheated and refluxed for three hours.

After cooling the mixture to room temperature after the reaction, after adding 100 ml of water and stirring for approximately one hour, the mixture was washed by liquid separation with water through a separation funnel to dry the organic layer and obtain a solid substance. The obtained solid substance was separated with a silica gel column (5 kg of $SiO_2$) to obtain a purple solid substance.

In so doing, 10 g of Compound i (5,6-dinitro-N,N,N', N'-tetraphenyl-benzo[1,2,5]thiadiazole) with an HPLC purity of 96% was obtained.

Furthermore, Compound j was obtained by performing the same synthesis as Synthesis A1-3 of Synthesis Example A1 described above using the obtained Compound i.

Compound k represented by Formula D-3 above was obtained by performing the same synthesis as Synthesis A1-4 as Synthesis Example A1 described above using the obtained Compound j.

In so doing, 3 g of Compound k (compound represented by Formula D-3 described above) with an HPLC purity of 99% which is a dark blue solid substance in external appearance was obtained. When Compound k was mass analyzed, Compound h was M+:622.

Furthermore, the obtained Compound k was purified by sublimation at a set temperature of 340° C. Compound k after the purification by sublimation had an HPLC purity of 99%.

2. Manufacture of Host Material (Tetracene-Based Material) Synthesis Example B1 Synthesis of Compound Represented by Formula H1-2

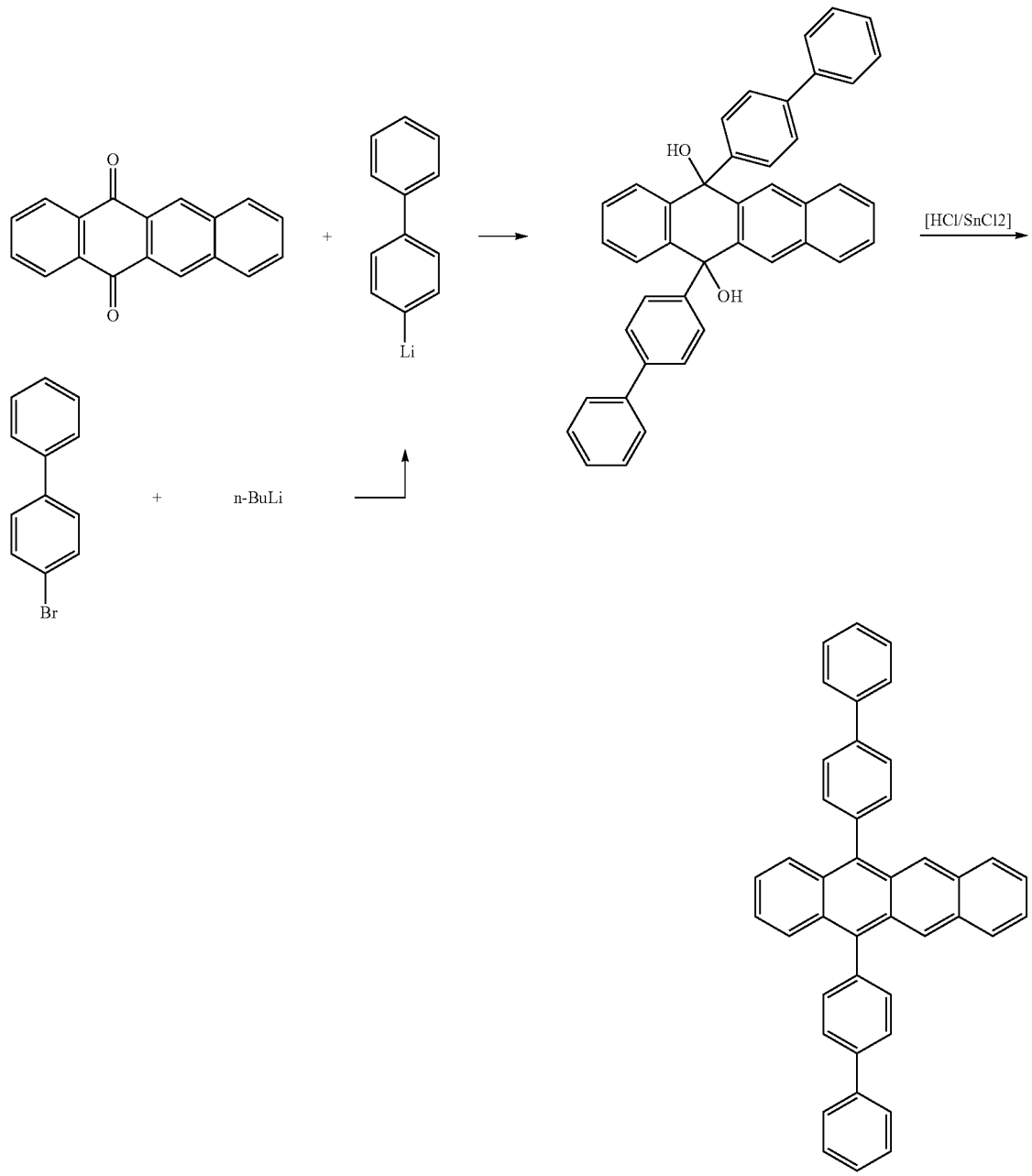

Synthesis B1-1

6 g of 4-bromobiphenyl and 50 ml of dry diethyl ether were poured into a 300 ml flask in an atmosphere of Ar. 14.5 ml of 1.6M n-BuLi/hexane solution was added dropwise at room temperature and reacted for 30 minutes.

Meanwhile, separately, 2.7 g of 5,12-naphthacenquinone and 100 ml of dry toluene were poured into a 500 ml flask in an atmosphere of Ar. Biphenyl lithium that was prepared in advance was added dropwise thereto and reacted for three hours. Following the reaction, after adding 20 ml of distilled water and stirring for 30 minutes, the mixture was placed in methanol to separate a solid substance through filtration. The obtained solid substance was purified by silica gel (500 g of $SiO_2$).

In so doing, 4.5 g of a white solid substance (5,12-bisbiphenyl-4-yl-5,12-naphthacene-5,12-diol) was obtained.

Synthesis B1-2

4.5 g of the diol substance obtained in Synthesis B1-1 and 300 ml of acetic acid were measured and poured into a 1000 ml flask. 5 g of hydrochloric acid (35%) in which 5 g of tin chloride (II) (anhydrous) had been dissolved was poured into the flask and stirred for 30 minutes. The mixture was then transferred to a separation funnel, before having toluene added, being washed by liquid separation using distilled water, and dried. The obtained solid substance was purified by a silica gel (500 g of SiO$_2$) to obtain 4 g of a yellow solid substance (compound represented by Formula H1-2) described above.

Synthesis Example B2

Synthesis of Compound Represented by Formula H1-5

Synthesis B2-1

6 g of 4-bromo-[1,1';3',1'']terphenyl and 50 ml of dry diethyl ether were poured into a 300 ml flask in an atmosphere of Ar. 14.5 ml of 1.6M n-BuLi/hexane solution was added dropwise at room temperature and reacted for 30 minutes.

Meanwhile, separately, 2 g of 5,12-naphthacenquinone and 100 ml of dry toluene were poured into a 500 ml flask in an atmosphere of Ar. Terphenyl lithium that had been prepared in advance was added dropwise thereto and reacted for three hours. Following the reaction, after adding 20 ml of

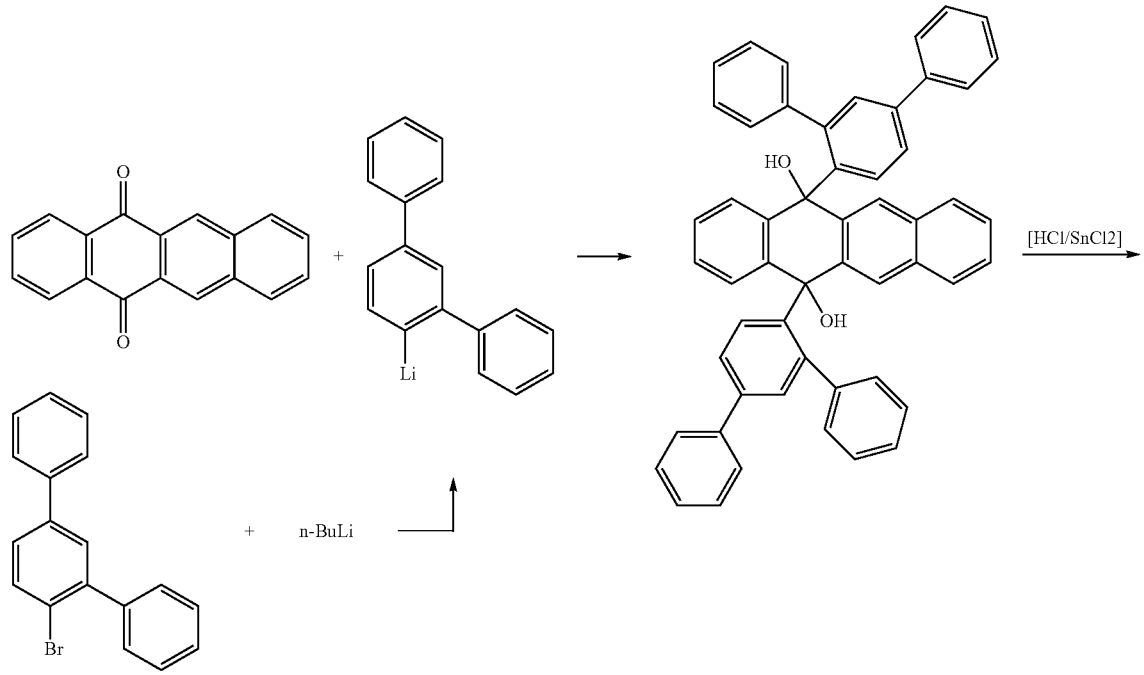

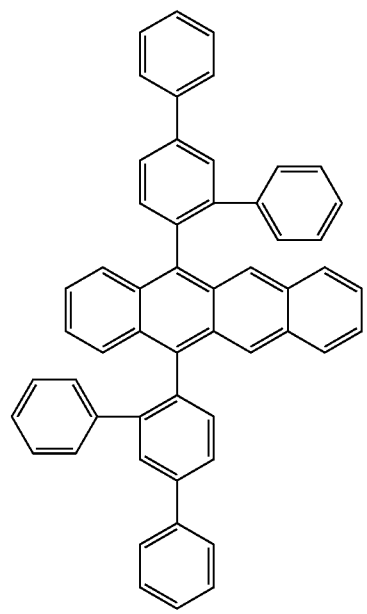

distilled water and stirring for 30 minutes, the mixture was placed in methanol to separate a solid substance through filtration. The obtained solid substance was purified by silica gel (500 g of $SiO_2$).

In so doing, 5 g of a white solid substance (5,12-bis-[1,1'; 3'0.1"]terphenyl-4'-yl-5,12-dihydronaphthacene-5,12-diol) was obtained.

Synthesis B2-2

5 g of the diol substance obtained in Synthesis B2-1 and 300 ml of acetic acid were measured and poured into a 1000 ml flask. 5 g of hydrochloric acid (35%) in which 5 g of tin chloride (II) (anhydrous) had been dissolved was poured into the flask and stirred for 30 minutes. The mixture was then transferred to a separation funnel, before having toluene added, being washed by liquid separation using distilled water, and dried. The obtained solid substance was purified by a silica gel (500 g of $SiO_2$) to obtain 4.5 g of a yellow solid substance (compound represented by Formula H1-5) described above.

Synthesis Example B3

Synthesis of Compound Represented by Formula H1-13

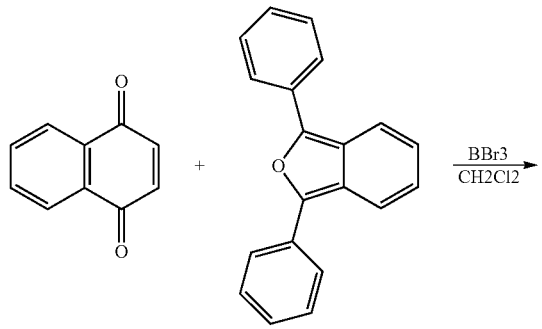

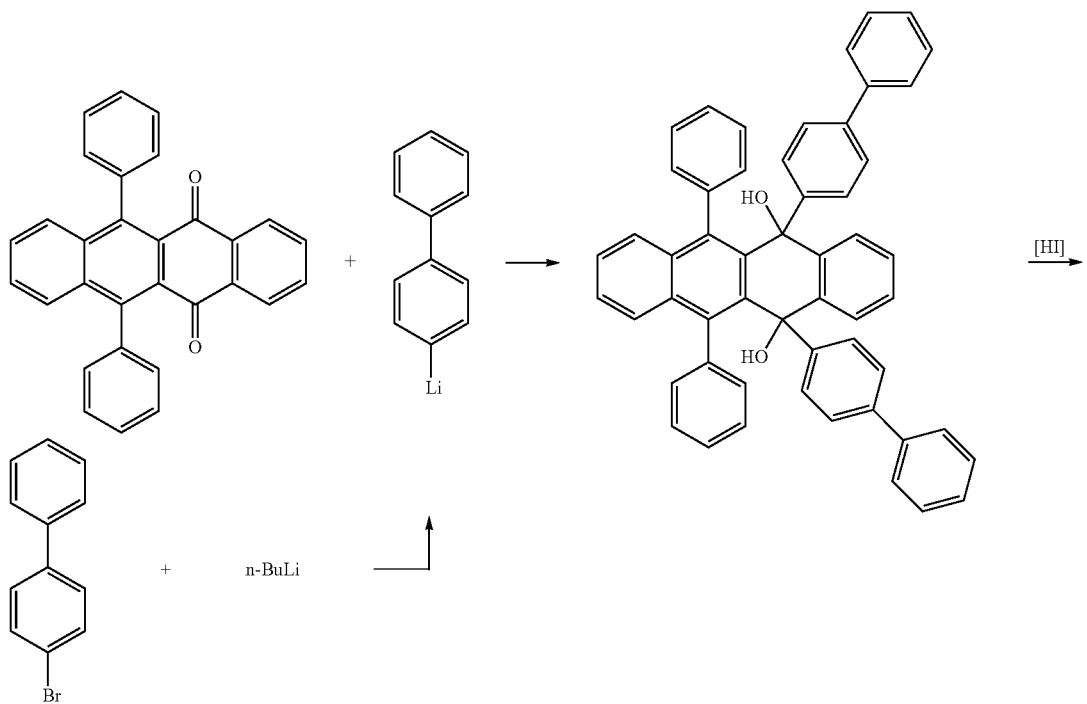

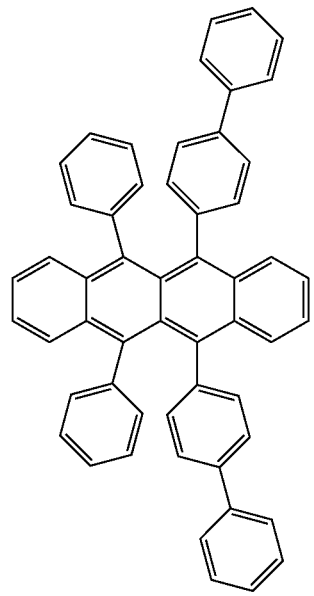

Synthesis B3-1

100 ml of dichloromethane, 5.2 g of naphthoquinone, and 10 g of 1,3-diphenylisobenzofuran were poured into a 500 ml flask and stirred for one hour. 7.1 g of yellow needle-shaped crystals (6,11-diphenyl-5,12-naphthacenequinone) was obtained by adding 33 ml of commercially available boron tribromide (1 mol/L of a dichloromethane solution) over ten minutes after the stirring.

Synthesis B3-2

6 g of 4-bromo-biphenyl and 80 ml of dry diethyl ether were poured into a 200 ml flask in an atmosphere of Ar. 16 ml of 1.6M n-BuLi/hexane solution was added dropwise at room temperature and reacted for 30 minutes.

Meanwhile, separately, 4.2 g of the quinone obtained in Synthesis B3-1 and 100 ml of dry toluene were poured into a 500 ml flask in an atmosphere of Ar. Biphenyl lithium that had been prepared in advance was added dropwise thereto and reacted for three hours. Following the reaction, after adding 20 ml of distilled water and stirring for 30 minutes, the mixture was placed in methanol to separate a solid substance through filtration. The obtained solid substance was purified by silica gel (500 g of $SiO_2$).

In so doing, 5.5 g of a white solid substance (5,12-bisbiphenyl-4-yl-6,11-diphenyl-5,12-dihydronaphthacene-5,12-diol) was obtained.

Synthesis B3-3

5 g of the diol substance obtained in Synthesis B3-2 and 200 ml of tetrahydrofuran were measured and poured into a 500 ml flask. 10 g of hydroiodic acid (55% aqueous solution) was poured into the flask and stirred for two hours while blocking light. The mixture was then transferred to a separation funnel, before having toluene added, being washed by liquid separation using distilled water, and dried. The obtained solid substance was purified by a silica gel (500 g of $SiO_2$) to obtain 3 g of a red solid substance (compound represented by Formula H1-13 described above).

3. Manufacture of Light Emitting Element

Example 1

(1) First, a transparent glass substrate with an average thickness of 0.5 mm was prepared. Next, an ITO electrode (anode) with an average thickness of 100 nm was formed on the substrate.

Furthermore, the substrate was soaked in order of acetone and 2-propanol, ultrasonically cleaned, oxygen plasma processed, and argon plasma processed. Such plasma processes were respectively performed in a state in which the substrate was heated to 70 to 90° C. at a plasma power of 100 W, a gas flow rate of 20 sccm, and for a processing time of 5 seconds.

(2) Next, an amine-based hole transport material (tetrakis-p-biphenylyl-benzidine) was deposited on the ITO electrode by a vacuum deposition method to form a hole transport layer with an average thickness of 50 nm.

(3) Next, the constituent material of the light emitting layer was deposited on the hole transport layer by a vacuum deposition method to form a light emitting layer with an average thickness of 25 nm. As the constituent material of the light emitting layer, the compound represented by Formula D-2 above was used as the light emitting material (guest material), and the compound represented by Formula H1-2 above (tetracene-based material) was used as the host material. Further, the content amount (doping concentration) of the light emitting material (dopant) within the light emitting layer was 4.0 wt %.

(4) Next, 2,9-dimethyl-4,7-diphenyl-1,10-phenanthroline (BCP) was formed on the light emitting layer by a vacuum deposition method to form an electron transport layer with an average thickness of 80 nm.

(5) Next, lithium fluoride (LiF) was formed on the electron transport layer by a vacuum deposition method to form an electron injection layer with an average thickness of 1 nm.

(6) Next, Al was formed on the electron injection layer by a vacuum deposition method. In so doing, a cathode that was configured by Al with an average thickness of 100 nm was formed.

(7) Next, a glass protective cover (sealing member) was placed to cover each of the layers that were formed, fixed by an epoxy resin, and sealed.

The light emitting element was manufactured by the processes described above.

Example 2

Other than using the compound represented by Formula H1-5 above (tetracene-based material) as the host material of the light emitting layer, the light emitting element was manufactured similarly to Example 1 described above.

Example 3

Other than using the compound represented by Formula H1-13 above (tetracene-based material) as the host material of the light emitting layer, the light emitting element was manufactured similarly to Example 1 described above.

Example 4

Other than making the content amount (doping concentration) of the light emitting material (dopant) within the light emitting layer 1.0 wt %, the light emitting element was manufactured similarly to Example 1 described above.

Example 5

Other than making the content amount (doping concentration) of the light emitting material (dopant) within the light emitting layer 2.0 wt %, the light emitting element was manufactured similarly to Example 1 described above.

Example 6

Other than making the content amount (doping concentration) of the light emitting material (dopant) within the light emitting layer 10.0 wt %, the light emitting element was manufactured similarly to Example 1 described above.

Example 7

Other than making the average thickness of the light emitting layer 15 nm and making the average thickness of the electron transport layer 90 nm, the light emitting element was manufactured similarly to Example 1 described above.

Example 8

Other than making the average thickness of the light emitting layer 50 nm and making the average thickness of the electron transport layer 55 nm, the light emitting element was manufactured similarly to Example 1 described above.

Example 9

Other than making the average thickness of the light emitting layer 70 nm and making the average thickness of the electron transport layer 35 nm, the light emitting element was manufactured similarly to Example 1 described above.

Example 10

Other than using the compound represented by Formula D-1 above as the light emitting material of the light emitting layer, the light emitting element was manufactured similarly to Example 1 described above.

Example 11

Other than using the compound represented by Formula D-3 above as the light emitting material of the light emitting layer, the light emitting element was manufactured similarly to Example 1 described above.

Reference Example

Other than using $Alq_3$ as the host material of the light emitting layer, the light emitting element was manufactured similarly to Example 1 described above.

4. Evaluation

For each Example and Reference Example, a constant current of 100 $mA/cm^2$ was applied using a constant current power source (KEITHLEY 2400 manufactured by TOYO Corporation), and the light emitting peak wavelength at this time was measured using a spectral radiant luminance meter (CS-2000 manufactured by Konica Minolta Sensing, Inc.). The light emitting power was measured using a light power measuring machine (Optical Power Meter 8230 manufactured by ADC Corporation). Here, S2000 manufactured by Ocean Optics, Inc. was used in the measurement of the light emitting peak wavelength of Reference Example.

Further, the voltage value (driving voltage) at this time was also measured.

Furthermore, the amount of time taken for the brightness to becomes 80% of the initial brightness (LT80) was measured.

Figure 5A:
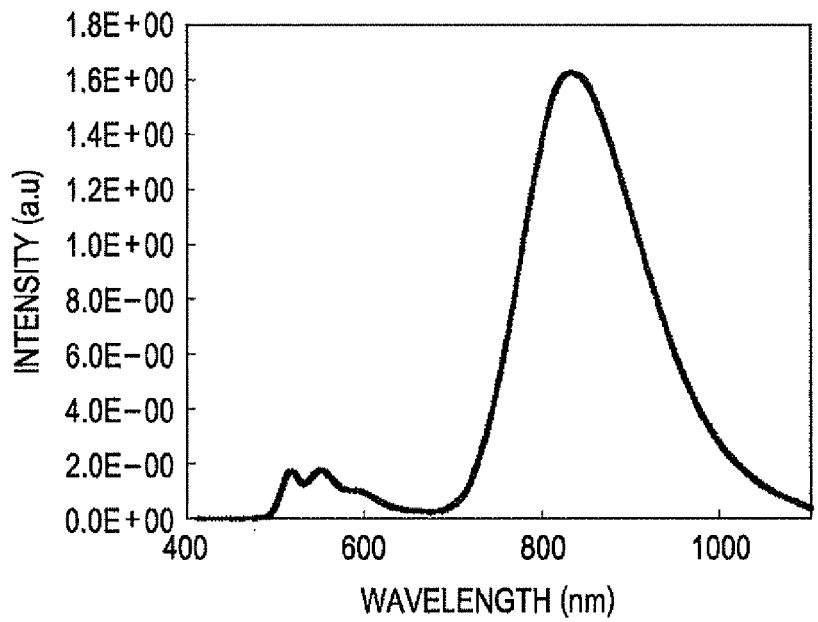
FIGS. 5A and 5B are diagrams that illustrate the light emitting spectra of light emitting elements according to an example (Example 1) and a reference example of the invention.
Figure 5B:
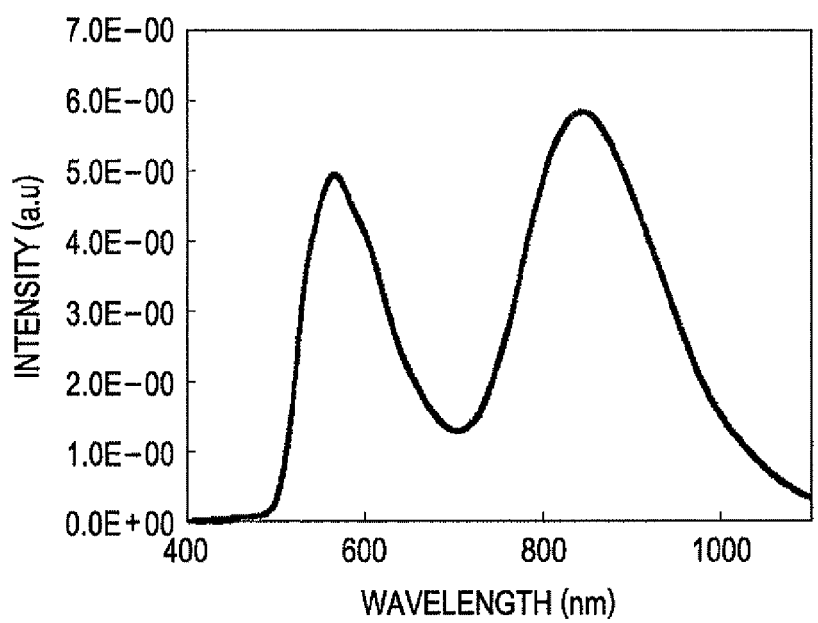

Such measurement results are shown in Table 1. Here, the light emitting spectrum of the light emitting element in Example 1 and Reference Example are shown in FIG. 5.

TABLE 1

| | | Light Emitting Layer | | | Electron Transport Layer | | Evaluation | | | |
| | | | | | | | Light Emitting Peak Wavelength [nm] | Light Emitting Power [mW/cm²] | Voltage [V] | LT80 [hr] |
| | Light Emitting Material | Host Material | Concentration of Light Emitting Material [w %] | Average Thickness [nm] | Material | Average Thickness [nm] | | | | |
| Example 1 | D-2 | H1-2 | 4 | 25 | BCP | 80 | 830 | 1.3 | 5.0 | 100 |
| Example 2 | D-2 | H1-5 | 4 | 25 | BCP | 80 | 830 | 1.3 | 5.0 | 130 |
| Example 3 | D-2 | H1-13 | 4 | 25 | BCP | 80 | 830 | 1.5 | 5.1 | 90 |
| Example 4 | D-2 | H1-2 | 1 | 25 | BCP | 80 | 820 | 1.2 | 4.9 | 90 |

TABLE 1-continued

| | Light Emitting Layer | | | | Electron Transport Layer | | Evaluation | | | |
| | | | | | | | Light Emitting | Light Emitting | | |
| | Light Emitting Material | Host Material | Concentration of Light Emitting Material [w %] | Average Thickness [nm] | Material | Average Thickness [nm] | Peak Wavelength [nm] | Power [mW/cm$^2$] | Voltage [V] | LT80 [hr] |
|---|---|---|---|---|---|---|---|---|---|---|
| Example 5 | D-2 | H1-2 | 2 | 25 | BCP | 80 | 825 | 1.2 | 5.0 | 100 |
| Example 6 | D-2 | H1-2 | 10 | 25 | BCP | 80 | 835 | 1.0 | 5.2 | 90 |
| Example 7 | D-2 | H1-2 | 4 | 15 | BCP | 90 | 830 | 1.3 | 4.8 | 80 |
| Example 8 | D-2 | H1-2 | 4 | 50 | BCP | 55 | 830 | 1.2 | 5.4 | 120 |
| Example 9 | D-2 | H1-2 | 4 | 70 | BCP | 35 | 830 | 1.2 | 5.7 | 120 |
| Example 10 | D-1 | H1-2 | 4 | 25 | BCP | 80 | 815 | 1.3 | 5.0 | 130 |
| Example 11 | D-3 | H1-2 | 4 | 25 | BCP | 80 | 880 | 0.9 | 5.1 | 110 |
| Reference Example | D-2 | Alq | 4 | 25 | BCP | 80 | 565, 840 | 0.3 | 6.6 | 20 |

As is clear from Table 1, the light emitting element of each Example emits light at near-infrared bands, and compared to the light emitting element of Reference Example, higher light emitting power is obtained. Further, compared to the light emitting element of Reference Example, the light emitting element of each Example can suppress the driving voltage. The light emitting element of each Example has excellent light emitting efficiency in such respects.

Further, compared to the light emitting element of Reference Example, the light emitting element of each Example has a long life.

This application claims priority from Japanese Patent Application No. 2011-092427 filed in the Japanese patent office on Apr. 18, 2011, the entire disclosure of which is hereby incorporated by reference in its entirely.

What is claimed is:

1. A thiadiazole-based compound represented by Formula 1 below:

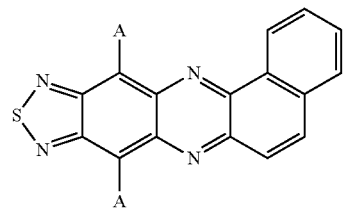

(1)

where in Formula 1, A indicates an aryl group, a diarylamino group, or triarylamine that may respectively independently include a hydrogen atom, an alkyl group, and a substituent.

2. A light emitting element compound comprising the thiadiazole-based compound according to claim 1.

3. A light emitting element comprising:
an anode;
a cathode; and
a light emitting layer that is provided between the anode and the cathode and that emits light through a passage of an electric current between the anode and the cathode,
wherein the light emitting element includes a host material and a compound represented by Formula 1 below as a light emitting material:

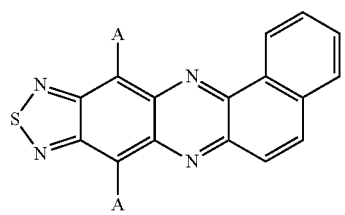

(1)

where in Formula 1, A indicates an aryl group, an arylamino group, or triarylamine that may respectively independently include a hydrogen atom, an alkyl group, and a substituent.

4. The light emitting element according to claim 3, wherein the light emitting layer includes a compound represented by Formula IRH-1 below as the host material:

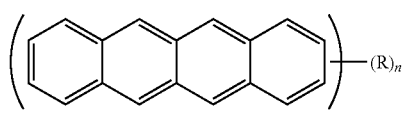

IRH-1 where in Formula IRH-1,
n indicates a natural number between 1 and 12, and
R represents a substituent or a functional group, and indicates an aryl group or an arylamino group that may respectively independently include a hydrogen atom, an alkyl group, and a substituent.

5. The light emitting element according to claim 3, wherein the light emitting layer includes a compound represented by Formula IRH-2 below as the host material:

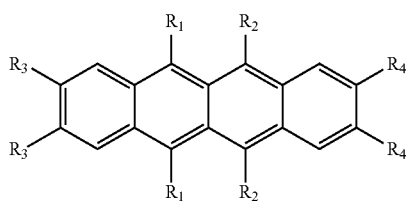

where in Formula IRH-2,

R$_1$ to R$_4$ indicate aryl groups or arylamino groups that may respectively independently include a hydrogen atom, an alkyl group, and a substituent, and R$_1$ to R$_4$ may be the same as or different from one another.

6. The light emitting element according to claim 3 wherein the light emitting element includes a compound represented by Formula IRH-3 below as the host material:

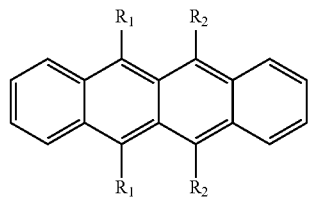

where in Formula IRH-3,

R$_1$ and R$_2$ indicate aryl groups or arylamino groups that may respectively independently include a hydrogen atom, an alkyl group, and a substituent, and R$_1$ and R$_2$ may be the same as or different from one another.

7. The light emitting element according to claim 3, wherein the host material consists of carbon atoms and hydrogen atoms.

8. A light emitting device comprising the light emitting element according to claim 3.

9. A light emitting device comprising the light emitting element according to claim 4.

10. A light emitting device comprising the light emitting element according to claim 5.

11. A light emitting device comprising the light emitting element according to claim 6.

12. An authentication device comprising the light emitting element according to claim 3.

13. An authentication device comprising the light emitting element according to claim 4.

14. An authentication device comprising the light emitting element according to claim 5.

15. An authentication device comprising the light emitting element according to claim 6.

16. An electronic apparatus comprising the light emitting element according to claim 3.

17. An electronic apparatus comprising the light emitting element according to claim 4.

18. An electronic apparatus comprising the light emitting element according to claim 5.

19. An electronic apparatus comprising the light emitting element according to claim 6.

* * * * *